(12) United States Patent　　　(10) Patent No.: US 7,728,129 B2
Mani et al.　　　(45) Date of Patent: Jun. 1, 2010

(54) PROCESSES FOR THE PREPARATION OF PIPERAZINYL AND DIAZAPANYL BENZAMIDE DERIVATIVES

(75) Inventors: Neelakandha S. Mani, San Diego, CA (US); David C. Palmer, Doylestown, PA (US); Chennagiri R. Pandit, San Diego, CA (US); Mayra B. Reyes, Somerset, NJ (US); Tong Xiao, Edison, NJ (US); Sergio Cesco-Cancian, Bethlehem, PA (US)

(73) Assignee: Janssen Pharmaceutica NV, Beerse (BE)

( * ) Notice: Subject to any disclaimer, the term of this patent is extended or adjusted under 35 U.S.C. 154(b) by 779 days.

(21) Appl. No.: 11/553,158

(22) Filed: Oct. 26, 2006

(65) Prior Publication Data

US 2007/0197508 A1　　Aug. 23, 2007

Related U.S. Application Data

(60) Provisional application No. 60/731,941, filed on Oct. 31, 2005.

(51) Int. Cl.
　　*C07D 413/10*　　(2006.01)
(52) U.S. Cl. .................................................. 544/121
(58) Field of Classification Search .................. 544/121
　　See application file for complete search history.

(56) References Cited

U.S. PATENT DOCUMENTS

| | | | |
|---|---|---|---|
| 6,548,670 B1 | 4/2003 | Burdeniue | |
| 7,414,047 B2 * | 8/2008 | Apodaca et al. | 514/217.05 |
| 2003/0163002 A1 | 8/2003 | Kramer | |
| 2004/0110746 A1 | 6/2004 | Apodaca et al. | |

FOREIGN PATENT DOCUMENTS

| | | |
|---|---|---|
| WO | WO 01/77064 | 10/2001 |
| WO | WO 2004/037801 | 5/2004 |

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Vippagunta et al. Advanced Drug Delivery Reviews, 48 (2001), pp. 3-26.*
PCT/US2006/041859 International Search Report, Apr. 25, 2007.
Ates-Alagoz, Z. et al. Synthesis of Some Novel Tetrahydronaphthalene Benzimidazole Derivatives. Het. Commun. 2001, 7(5), 455-460.
Beke, D. et al. Eine neue Synthese des N-Isopropyl-nor-adrenalins. Pharmazeutische Zentralhalle fuer Deutschland 1953, 92, 237-241. (English language abstract provided.).

Kjell, D.P. et al. A Novel, Nonaqueous Method for Regenration of Aldehydes from Bisulfite Adducts. J. Org. Chem. 1999, 64, 5722-5724.

(Continued)

*Primary Examiner*—Rebecca L Anderson
*Assistant Examiner*—Matthew P Coughlin
(74) *Attorney, Agent, or Firm*—Michael J. Atkins

(57) ABSTRACT

The present invention is directed to novel processes for the preparation of substituted piperazinyl and diazepanyl benzamides of formula (I), as defined in the specification, useful for the treatment of disorders and conditions mediated by the histamine receptor.

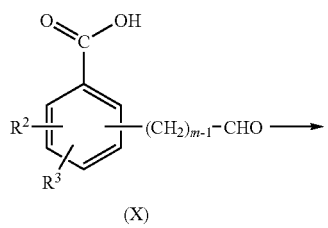

(X)

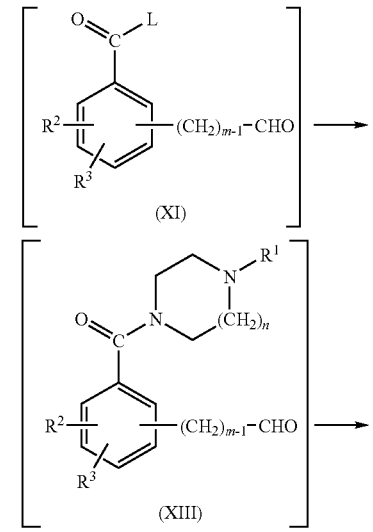

(XI)

(XIII)

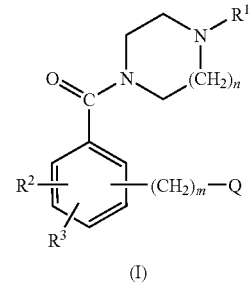

(I)

7 Claims, No Drawings

OTHER PUBLICATIONS

Johnson, T.J. et al. The Chemistry of Terpenes—VIII. Characterisation of the Bisulphite Adducts of α,β-Unsaturated Aldehydes by NMR Spectroscopy. Tetrahedron 1978, 34, 547-551.

Mitra, A.K. et al. Regeneration of Aldehydes from Bisulfite Addition Products in the Solid State using Montmorillonite KSF Clay under Microwave Irradiation. J. Chem. Research (S) 1999, 9, 560-561.

Paglietti, G. et al. Preparazione e Attivita' Farmacologica di 2-(4'R')Feni1-5R-Benzimidazoli e 2-(4'Piridinil)-5R-Benzimidazoli. Il Farmaco 1988, 43(3), 215-226. (English language abstract provided.).

Ragan, J.A. et al. Safe Execution of a Large-Scale Ozonolysis: Preparation of the Bisulfite Adduct of 2-Hydroxyindan-2-carboxaldehyde and Its Utility in a Reductive Amination. Org. Process Res. Dev. 2003, 7, 155-160.

Ridley, H.F. et al. A New Synthesis of Benzimidazoles and Aza-analogs. J. Het. Chem. 1965, 2(4), 453-456.

Servi, S. et al. A Novel and Efficient Synthesis of 3-Aryl and 3-Heteroaryl Substituted-1H-Indazoles and Their Mannich Derivatives. Synth. Commun. 2002, 33(22), 3399-3405.

Shaikh, I.A. et al. Streptonigrin. 1. Structure-Activity Relationships among Simple Bicyclic Analogues. Rate Dependence of DNA Degradation on Quinone Reduction Potential. J. Med. Chem. 1986, 29, 1329-1340.

Temple, Jr., C. et al. Synthesis of Potential Anticancer Agents: Imidazo[4,5-c]pyridines and Imidazo[4,5-b]pyridines. J. Med. Chem. 1987, 30, 1746-1751.

von der Saal, W. et al. Nonsteroidal Cardiotonics. 2. The Inotropic Activity of Linear, Tricyclic 5-6-5 Fused Heterocycles. J . Med. Chem. 1989, 32, 1481-1491.

* cited by examiner

PROCESSES FOR THE PREPARATION OF PIPERAZINYL AND DIAZAPANYL BENZAMIDE DERIVATIVES

CROSS REFERENCE TO RELATED APPLICATIONS

This application claims the benefit of U.S. Provisional Application 60/731,941 filed on Oct. 31, 2005, which is incorporated by reference herein in its entirety.

FIELD OF THE INVENTION

The present invention relates to processes for the preparation of piperazinyl and diazepanyl benzamide derivatives, useful for the treatment of disorders and conditions mediated by the histamine receptor.

BACKGROUND OF THE INVENTION

US Patent Application Publication 2004-0110746 A1, published Apr. 21, 2005 (also published as PCT Publication WO 04/037801, May 6, 2004), which is hereby incorporated by reference, discloses novel piperazinyl and diazepanyl benzamide derivatives useful for the treatment of histamine receptor mediated disorders. More specifically, the compounds are useful for the treatment of disorders and conditions mediated by the $H_3$ receptor. More particularly, the compounds are useful for treating or preventing neurologic disorders including sleep/wake and arousal/vigilance disorders (e.g. insomnia and jet lag), attention deficit hyperactivity disorders (ADHD), learning and memory disorders, cognitive dysfunction, migraine, neurogenic inflammation, dementia, mild cognitive impairment (pre-dementia), Alzheimer's disease, epilepsy, narcolepsy, eating disorders, obesity, motion sickness, vertigo, schizophrenia, substance abuse, bipolar disorders, manic disorders and depression, as well as other histamine $H_3$ receptor mediated disorders such as upper airway allergic response, asthma, itch, nasal congestion and allergic rhinitis in a subject in need thereof. For example, methods for preventing, inhibiting the progression of, or treating upper airway allergic response, asthma, itch, nasal congestion and allergic rhinitis.

US Patent Application Publication 2004-0110746 A1, published Apr. 21, 2005 (also published as PCT Publication WO 04/037801, May 6, 2004) discloses a process for the preparation of the piperazinyl and diazepanyl benzamides. There remains a need for processes for the preparation of piperazinyl and diazepanyl benzamide derivatives that are suitable for large scale/commercial applications.

SUMMARY OF THE INVENTION

The present invention is directed to a process for the preparation of compounds of formula (I)

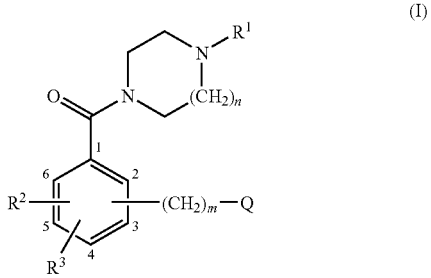

(I)

and pharmaceutically acceptable salts, esters, tautomers, solvates or amides thereof;

wherein $R^1$ is selected from the group consisting of $C_{1-10}$alkyl, $C_{3-8}$alkenyl, $C_{3-8}$cycloalkyl, $(C_{3-8}$ cycloalkyl$)C_{1-6}$ alkyl, $(C_{3-8}$cycloalkyl$)C_{3-8}$alkenyl and $(C_{1-8}$alkylcarbonyl$)C_{1-8}$alkyl;

n is an integer from 1 to 2;

$R^2$ and $R^3$ are each independently selected from hydrogen, fluoro, chloro, bromo, nitro, trifluoromethyl, methyl, or $C_{1-3}$alkoxy;

m is an integer from 1 to 7; (preferably, m is an integer from 1 to 4, more preferably, m is 1);

Q is $NR^8R^9$;

wherein $R^8$ is selected from the group consisting of hydrogen, $C_{1-6}$alkyl, $C_{3-6}$alkenyl, 3-9 membered carbocyclyl, 3-12 membered heterocyclyl (preferably 5-9 or 5-8-membered heterocyclyl), phenyl, (6-9-membered heterocyclyl)$C_{1-6}$alkylene and (phenyl)$C_{1-6}$alkylene;

and $R^9$ is selected from the group consisting of $C_{1-6}$alkyl, $C_{3-6}$alkenyl, 6-9 membered carbocyclyl, 3-12 membered heterocyclyl (preferably 5-9 or 5-8-membered heterocyclyl), phenyl, (6-9-membered heterocyclyl)$C_{1-6}$alkylene, and (phenyl)$C_{1-6}$ alkylene;

alternatively, Q is a saturated 3-12 membered N-linked heterocyclyl, wherein, in addition to the N-linking nitrogen, the 3-12 membered heterocyclyl may optionally contain between 1 and 3 additional heteroatoms independently selected from O, S, and NH;

wherein Q (when Q is a saturated 3-12 membered N-linked heterocyclyl) is optionally substituted with 1-3 substituents independently selected from the group consisting of hydroxy, halo, carboxamide, $C_{1-6}$alkyl, 5-9 membered or 6-9 membered heterocyclyl, —N($C_{1-6}$ alkyl)(5-9 membered or 6-9 membered heterocyclyl), —NH(5-9 membered or 6-9 membered heterocyclyl), —O(5-9 or 6-9 membered heterocyclyl), (5-9 membered or 6-9 membered heterocyclyl)$C_{1-3}$alkylene, $C_{1-6}$alkoxy, ($C_{3-6}$cycloalkyl)-O—, phenyl, (phenyl)$C_{1-3}$alkylene, and (phenyl)$C_{1-3}$alkylene-O—;

where each of the above heterocyclyl, phenyl, and alkyl groups may be further optionally substituted with from 1 to 3 substituents independently selected from the group consisting of trifluoromethyl, methoxy, halo, nitro, cyano, hydroxy and $C_{1-3}$alkyl;

provided that the 5- and 6-positions on the phenyl ring are unsubstituted (i.e., the $R^2$, $R^3$ and —$(CH_2)_m$-Q are bound to the 2-, 3- and 4-positions on the phenyl ring);

provided further that when $R^1$ is methyl, then —$(CH_2)_m$-Q is not piperidin-1-ylmethyl;

and wherein each of the above alkyl, alkylene, alkenyl, heterocyclyl, cycloalkyl, carbocyclyl, and aryl groups may each be independently and optionally substituted with between 1 and 3 substituents independently selected from the group consisting of trifluoromethyl, methoxy, halo, amino, nitro, hydroxy and $C_{1-3}$ alkyl;

comprising

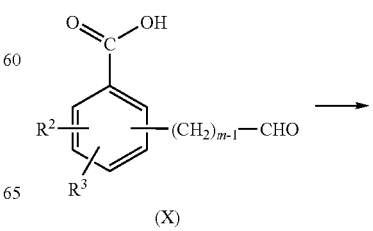

(X)

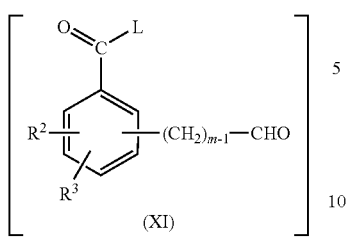

(XI)

reacting a compound of formula (X); in a first organic solvent; to yield the corresponding compound of formula (XI), wherein L is a leaving group; and wherein the compound of formula (XI) is not isolated;

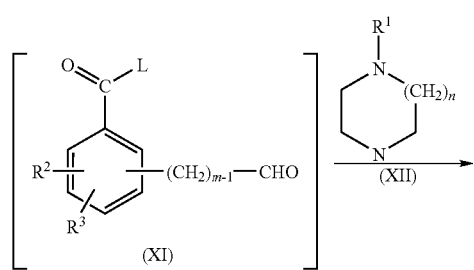

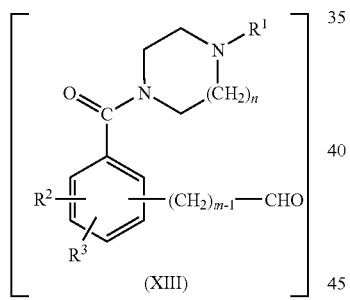

(XIII)

reacting the compound of formula (XI) with a compound of formula (XII); in the presence of an organic or inorganic base; in a second organic solvent; to yield the corresponding compound of formula (XIII); wherein the compound of formula (XIII) is not isolated;

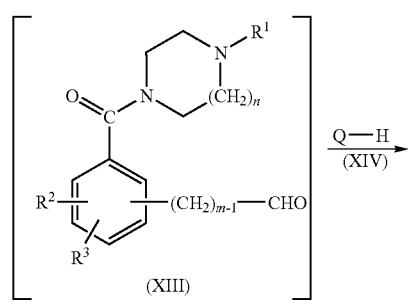

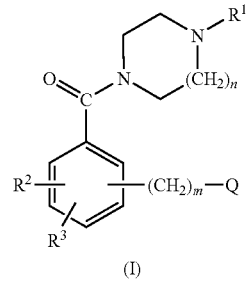

(I)

and reacting the compound of formula (XIII) with a compound of formula (XIV); in the presence of a reducing agent; in a third organic solvent; to yield the corresponding compound of formula (I).

The present invention is further directed to improvements to an alternate process for the preparation of compounds of formula (I)

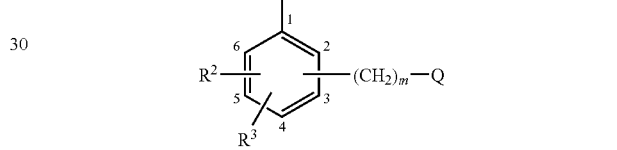

and pharmaceutically acceptable salts, esters, tautomers, solvates or amides thereof;

wherein $R^1$ is selected from the group consisting of $C_{1-10}$alkyl, $C_{3-8}$ alkenyl, $C_{3-8}$cycloalkyl, ($C_{3-8}$ cycloalkyl)$C_{1-6}$ alkyl, ($C_{3-8}$ cycloalkyl)$C_{3-8}$ alkenyl and ($C_{1-8}$alkylcarbonyl)$C_{1-8}$ alkyl;

n is an integer from 1 to 2;

$R^2$ and $R^3$ are each independently selected from hydrogen, fluoro, chloro, bromo, nitro, trifluoromethyl, methyl, or $C_{1-3}$alkoxy;

m is an integer from 1 to 7; (preferably, m is an integer from 1 to 4, more preferably, m is 1);

Q is $NR^8R^9$;

wherein $R^8$ is selected from the group consisting of hydrogen, $C_{1-6}$alkyl, $C_{3-6}$alkenyl, 3-9 membered carbocyclyl, 3-12 membered heterocyclyl (preferably 5-9 or 5-8-membered heterocyclyl), phenyl, (6-9-membered heterocyclyl)$C_{1-6}$ alkylene and (phenyl)$C_{1-6}$alkylene;

and $R^9$ is selected from the group consisting of $C_{1-6}$alkyl, $C_{3-6}$alkenyl, 6-9 membered carbocyclyl, 3-12 membered heterocyclyl (preferably 5-9 or 5-8-membered heterocyclyl), phenyl, (6-9-membered heterocyclyl)$C_{1-6}$alkylene, and (phenyl)$C_{1-6}$ alkylene;

alternatively, Q is a saturated 3-12 membered N-linked heterocyclyl, wherein, in addition to the N-linking nitrogen, the 3-12 membered heterocyclyl may optionally contain between 1 and 3 additional heteroatoms independently selected from O, S, and NH;

wherein Q (when Q is a saturated 3-12 membered N-linked heterocyclyl) is optionally substituted with 1-3 substituents independently selected from the group consisting of hydroxy, halo, carboxamide, $C_{1-6}$alkyl, 5-9 membered or 6-9 membered heterocyclyl, —N($C_{1-6}$ alkyl)(5-9 membered or 6-9 membered heterocyclyl), —NH(5-9 membered or 6-9 membered heterocyclyl), —O(5-9 or 6-9 membered heterocyclyl), (5-9 membered or 6-9 membered heterocyclyl)$C_{1-3}$alkylene, $C_{1-6}$alkoxy, ($C_{3-6}$cycloalkyl)-O—, phenyl, (phenyl)$C_{1-3}$ alkylene, and (phenyl)$C_{1-3}$alkylene-O—;

where each of the above heterocyclyl, phenyl, and alkyl groups may be further optionally substituted with from 1 to 3 substituents independently selected from the group consisting of trifluoromethyl, methoxy, halo, nitro, cyano, hydroxy and $C_{1-3}$alkyl;

provided that the 5- and 6-positions on the phenyl ring are unsubstituted (i.e., the $R^2$, $R^3$ and —$(CH_2)_m$-Q are bound to the 2-, 3- and 4-positions on the phenyl ring);

provided further that when $R^1$ is methyl, then —$(CH_2)_m$-Q is not piperidin-1-ylmethyl;

and wherein each of the above alkyl, alkylene, alkenyl, heterocyclyl, cycloalkyl, carbocyclyl, and aryl groups may each be independently and optionally substituted with between 1 and 3 substituents independently selected from the group consisting of trifluoromethyl, methoxy, halo, amino, nitro, hydroxy and $C_{1-3}$ alkyl;

comprising

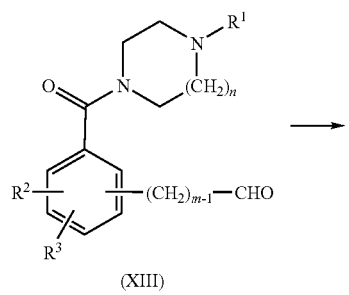

(XIII)

reacting a compound of formula (XIII) with a source of bisulfite; in a polar organic solvent; to yield the corresponding compound of formula (XVII);

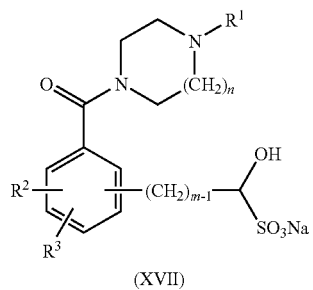

(XVII)

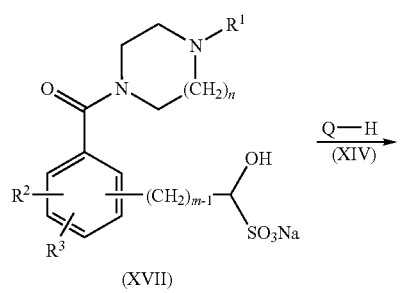

(XVII)

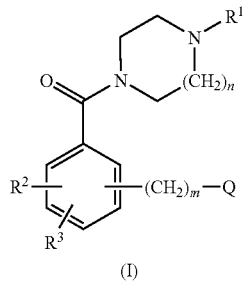

(I)

and reacting the compound of formula (XVII) with a compound of formula (XIV); in the presence of a reducing agent; in the presence of an organic or inorganic base; in an organic solvent; to yield the corresponding compound of formula (I).

The present invention is further directed to improvements to an alternate process for the preparation of compounds of formula (I)

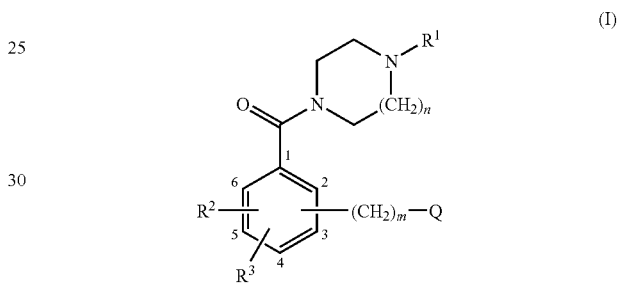

and pharmaceutically acceptable salts, esters, tautomers, solvates or amides thereof;

wherein $R^1$ is selected from the group consisting of $C_{1-10}$alkyl, $C_{3-8}$ alkenyl, $C_{3-8}$cycloalkyl, ($C_{3-8}$ cycloalkyl)$C_{1-6}$ alkyl, ($C_{3-8}$cycloalkyl)$C_{3-8}$ alkenyl and ($C_{1-8}$alkylcarbonyl)$C_{1-8}$alkyl;

n is an integer from 1 to 2;

$R^2$ and $R^3$ are each independently selected from hydrogen, fluoro, chloro, bromo, nitro, trifluoromethyl, methyl, or $C_{1-3}$alkoxy;

m is an integer from 1 to 7; (preferably, m is an integer from 1 to 4, more preferably, m is 1);

Q is $NR^8R^9$;

wherein $R^8$ is selected from the group consisting of hydrogen, $C_{1-6}$alkyl, $C_{3-6}$alkenyl, 3-9 membered carbocyclyl, 3-12 membered heterocyclyl, phenyl, (6-9-membered heterocyclyl)$C_{1-6}$alkylene and (phenyl)$C_{1-6}$alkylene;

and $R^9$ is selected from the group consisting of $C_{1-6}$alkyl, $C_{3-6}$alkenyl, 6-9 membered carbocyclyl, 3-12 membered heterocyclyl, phenyl, (6-9-membered heterocyclyl)$C_{1-6}$alkylene, and (phenyl)$C_{1-6}$ alkylene;

alternatively, Q is a saturated 3-12 membered N-linked heterocyclyl, wherein, in addition to the N-linking nitrogen, the 3-12 membered heterocyclyl may optionally contain between 1 and 3 additional heteroatoms independently selected from O, S, and NH;

wherein Q (when Q is a saturated 3-12 membered N-linked heterocyclyl) is optionally substituted with 1-3 substituents independently selected from the group consisting of hydroxy, halo, carboxamide, $C_{1-6}$alkyl, 5-9 membered or 6-9 membered heterocyclyl, —N($C_{1-6}$ alkyl)(5-9 membered or 6-9 membered heterocyclyl), —NH(5-9 membered or 6-9 membered heterocyclyl), —O(5-9 or 6-9 membered heterocyclyl), (5-9 membered or 6-9 membered heterocyclyl)$C_{1-3}$alkylene, $C_{1-6}$alkoxy, $(C_{3-6}$cycloalkyl)-O—, phenyl, (phenyl)$C_{1-3}$ alkylene, and (phenyl)$C_{1-3}$alkylene-O—;

where each of the above heterocyclyl, phenyl, and alkyl groups may be further optionally substituted with from 1 to 3 substituents independently selected from the group consisting of trifluoromethyl, methoxy, halo, nitro, cyano, hydroxy and $C_{1-3}$alkyl;

provided that the 5- and 6-positions on the phenyl ring are unsubstituted (i.e., the $R^2$, $R^3$ and —$(CH_2)_m$-Q are bound to the 2-, 3- and 4-positions on the phenyl ring);

provided further that when $R^1$ is methyl, then —$(CH_2)_m$-Q is not piperidin-1-ylmethyl;

and wherein each of the above alkyl, alkylene, alkenyl, heterocyclyl, cycloalkyl, carbocyclyl, and aryl groups may each be independently and optionally substituted with between 1 and 3 substituents independently selected from the group consisting of trifluoromethyl, methoxy, halo, amino, nitro, hydroxy and $C_{1-3}$ alkyl;

comprising

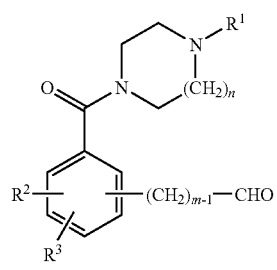

(XIII)

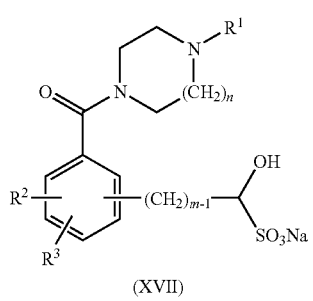

(XVII)

reacting a compound of formula (XIII) with a source of bisulfite; in a polar organic solvent; to yield the corresponding compound of formula (XVII);

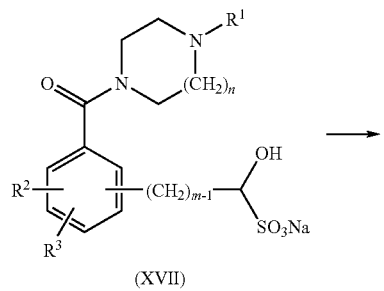

(XVII)

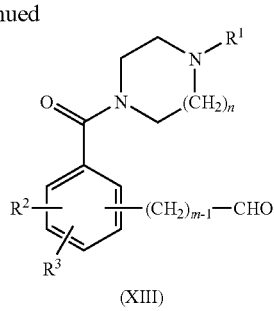

(XIII)

reacting the compound of formula (XVII) with an organic or inorganic base; in an organic solvent; to yield the corresponding compound of formula (XIII);

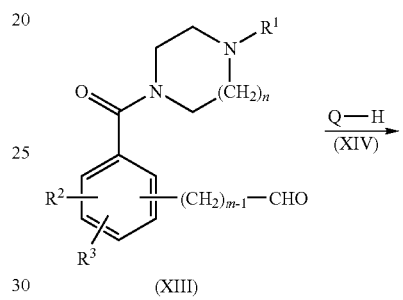

(XIII)

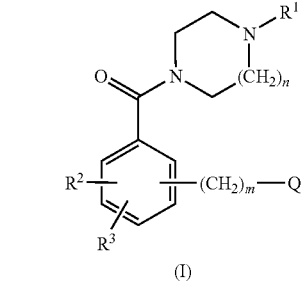

(I)

and reacting the compound of formula (XIII) with a compound of formula (XIV); in the presence of a reducing agent; in an organic solvent; to yield the corresponding compound of formula (I).

In an embodiment, the present invention is directed to processes for the preparation of compounds of formula (Ia)

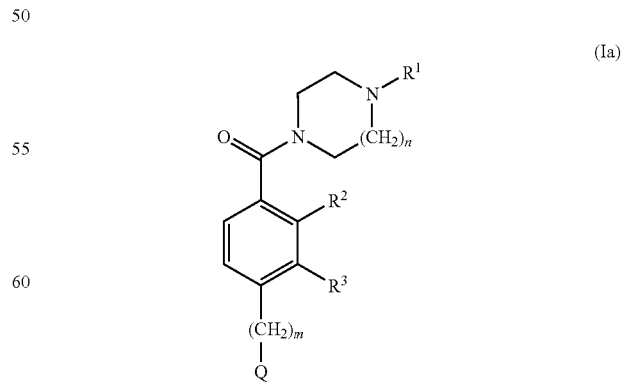

and pharmaceutically acceptable salts, esters, tautomers, solvates or amides thereof.

In another embodiment, the present invention is directed to processes for the preparation of a compound of formula (Is)

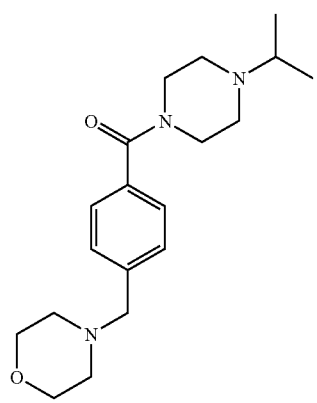

(Is)

also known as (4-isopropyl-piperazin-1-yl)-(4-morpholin-4-ylmethyl-phenyl)-methanone, or a pharmaceutically acceptable salt, ester, tautomer, solvate or amide thereof.

The present invention is further directed to novel crystalline salts of the compound of formula (I). In an embodiment, the present invention is directed to a maleate, succinate, fumarate, hydrochloride or hydrobromode salt of the compound of formula (I).

In an embodiment, the present invention is directed to novel crystalline salts of the compound of formula (Is). In an embodiment, the present invention is directed to a maleate, succinate, fumarate, hydrochloride or hydrobromide salt of the compound of formula (Is). In another embodiment, the present invention is directed to a crystalline succinate salt of the compound of formula (Is). In another embodiment, the present invention is directed to a crystalline mono-succinate salt of the compound of formula (Is).

The present invention is further directed to a product prepared according to any of the processed described herein.

Illustrative of the invention is a pharmaceutical composition comprising a pharmaceutically acceptable carrier and a succinate salt of the compound of formula (Is) as described herein. An illustration of the invention is a pharmaceutical composition made by mixing a succinate salt of the compound of formula (Is) as described herein and a pharmaceutically acceptable carrier. Illustrating the invention is a process for making a pharmaceutical composition comprising mixing a succinate salt of the compound of formula (Is) as described herein and a pharmaceutically acceptable carrier.

Illustrative of the invention is a pharmaceutical composition comprising a pharmaceutically acceptable carrier and a product prepared according to any of the processes described herein. An illustration of the invention is a pharmaceutical composition made by mixing a product prepared according to any of the processes described herein and a pharmaceutically acceptable carrier. Illustrating the invention is a process for making a pharmaceutical composition comprising mixing a product prepared according to any of the processes described herein and a pharmaceutically acceptable carrier.

Exemplifying the invention are methods of treating a disorder mediated by histamine, preferably, the $H_3$ histamine receptor, (selected from the group consisting of neurologic disorders including sleep/wake and arousal/vigilance disorders (e.g. insomnia and jet lag), attention deficit hyperactivity disorders (ADHD), learning and memory disorders, cognitive dysfunction, migraine, neurogenic inflammation, dementia, mild cognitive impairment (pre-dementia), Alzheimer's disease, epilepsy, narcolepsy, eating disorders, obesity, motion sickness, vertigo, schizophrenia, substance abuse, bipolar disorders, manic disorders and depression, as well as other histamine $H_3$ receptor mediated disorders such as upper airway allergic response, asthma, itch, nasal congestion and allergic rhinitis) comprising administering to a subject in need thereof, a therapeutically effective amount of a succinate salt of the compound of formula (Is) as described herein or pharmaceutical composition comprising a succinate salt of the compound of formula (Is) as described above.

Exemplifying the invention are methods of treating a disorder mediated by histamine, preferably, the $H_3$ histamine receptor, (selected from the group consisting of neurologic disorders including sleep/wake and arousal/vigilance disorders (e.g. insomnia and jet lag), attention deficit hyperactivity disorders (ADHD), learning and memory disorders, cognitive dysfunction, migraine, neurogenic inflammation, dementia, mild cognitive impairment (pre-dementia), Alzheimer's disease, epilepsy, narcolepsy, eating disorders, obesity, motion sickness, vertigo, schizophrenia, substance abuse, bipolar disorders, manic disorders and depression, as well as other histamine $H_3$ receptor mediated disorders such as upper airway allergic response, asthma, itch, nasal congestion and allergic rhinitis) comprising administering to a subject in need thereof, a therapeutically effective amount of a product prepared according to any of the processes described herein or a pharmaceutical composition as described above.

Another example of the invention is the use of a succinate salt of the compound of formula (Is) or a product prepared according to any of the processes described herein in the preparation of a medicament for treating: (a) a sleep/wake disorder, (b) an arousal/vigilance disorders, (c) insomnia, (d) jet lag, (e) attention deficit hyperactivity disorders (ADHD), (f) a learning disorder, (g) a memory disorder, (h) cognitive dysfunction, (i) migraine, (j) neurogenic inflammation, (k) dementia, (l) mild cognitive impairment (pre-dementia), (m) Alzheimer's disease, (n) epilepsy, (o) narcolepsy, (p) an eating disorder, (q) obesity, (r) motion sickness, (s) vertigo, (t) schizophrenia, (u) substance abuse, (v) bipolar disorder, (w) manic disorder, (x) depression, (y) upper airway allergic response, (z) asthma, (aa) itch, (bb) nasal congestion or (cc) allergic rhinitis, in a subject in need thereof.

DETAILED DESCRIPTION OF THE INVENTION

The present invention is directed to processes for the preparation of compounds of formula (I)

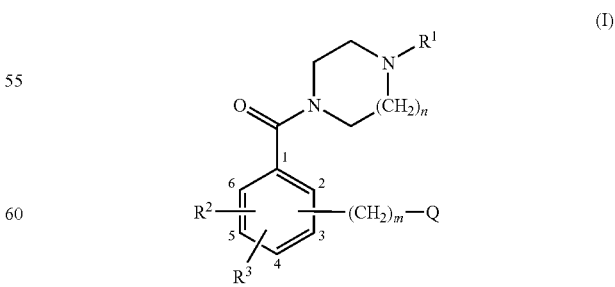

(I)

wherein n, $R^1$, $R^2$, $R^3$, m and Q are as herein defined, useful for the treatment of disorders and conditions modulated by a histamine receptor.

As used herein, "$C_{a-b}$" (where a and b are integers) refers to a radical containing from a to b carbon atoms inclusive. For example, $C_{1-3}$ denotes a radical containing 1, 2 or 3 carbon atoms.

As used herein, "halo" or "halogen" shall mean monovalent radicals of chlorine, bromine, fluorine and iodine.

As used herein, the term "alkyl", whether used alone or as part of a substituent group, shall include straight and branched saturated carbon chains. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1-4 carbon atoms. "Alkylene" refers to a bivalent hydrocarbyl group, such as methylene (—$CH_2$—), ethylene (—$CH_2$—$CH_2$—) or propylene (—$CH_2CH_2CH_2$—), and so on.

As used herein, the term "alkylene" refers to a divalent straight- or branched-chain alkyl group. Suitable examples include, but are not limited to methylene, ethylene, n-propylene, and the like.

As used herein, unless otherwise noted, "alkenyl" shall mean an alkylene group with at least two hydrogen atoms replaced with a pi bond to form a carbon-carbon double bond, such as propenyl, butenyl, pentenyl, and so on. Where the alkenyl group is $R^8$ or $R^9$, the open radical (point of attachment to the rest of the molecule) is on $sp^3$ carbon, as illustrated by allyl, and the double bond or bonds is therefore at least alpha (if not beta, gamma, etc.) to the open radical.

As used herein, "alkylidene" refers to a saturated or unsaturated, branched, straight-chain or cyclic divalent hydrocarbon radical derived by removal of two hydrogen atoms from the same carbon atom of a parent alkane, alkene or alkyne. The divalent radical center forms a double bond with a single atom on the rest of the molecule. Typical alkylidene radicals include, but are not limited to, ethanylidene; propylidenes such as propan-1-ylidene, propan-2-ylidene, cyclopropan-1-ylidene; butylidenes such as butan-1-ylidene, butan-2-ylidene, 2-methyl-propan-1-ylidene, cyclobutan-1-ylidene; and the like.

As used herein, unless otherwise noted, "alkoxy" shall denote an oxygen ether radical of the above-described straight or branched chain alkyl groups. For example, methoxy, ethoxy, n-propoxy, sec-butoxy, t-butoxy, n-hexyloxy and the like.

As used herein, unless otherwise noted, "cycloalkyl" shall denote a three- to eight-membered, saturated monocyclic carbocyclic ring structure. Suitable examples include cyclopropyl, cyclobutyl, cyclopentyl, cyclohexyl, cycloheptyl and cyclooctyl.

As used herein, unless otherwise noted, "cycloalkenyl" shall denote a three- to eight-membered, partially unsaturated, monocyclic, carbocyclic ring structure, wherein the ring structure contains at least one double bond. Suitable examples include cyclohexenyl, cyclopentenyl, cycloheptenyl, cyclooctenyl, cyclohex-1,3-dienyl and the like.

As used herein, unless otherwise noted, "aryl" shall refer to carbocyclic aromatic groups such as phenyl, naphthyl, and the like. Divalent radicals include phenylene (—$C_6H_4$—) which is preferably phen-1,4-diyl, but may also be phen-1,3-diyl.

As used herein, unless otherwise noted, "aralkyl" shall mean any alkyl group substituted with an aryl group such as phenyl, naphthyl, and the like. Examples of aralkyls include benzyl, phenethyl, and phenylpropyl.

As used herein, unless otherwise noted, "carbocyclyl" shall mean any cyclic group consisting of 3-12 carbon atoms, and preferably 6-9 carbon atoms, in the skeleton ring or rings, if the carbocycle is a fused or spiro bicyclic or tricyclic group.

A carbocycle may be saturated, unsaturated, partially unsaturated, or aromatic. Examples include cycloalkyl, cycloalkenyl, cycloalkynyl; specific examples include phenyl, benzyl, indanyl, and biphenyl. A carbocycle may have substituents that are not carbon or hydrogen, such as hydroxy, halo, halomethyl, and so on as provided elsewhere herein.

As used herein, unless otherwise noted, the terms "heterocycle", "heterocyclyl" and "heterocyclo" shall denote any three-, four-, five-, six-, seven-, or eight-membered monocyclic, nine- or ten-membered bicyclic, or thirteen- or fourteen-membered tricyclic ring structure containing at least one heteroatom moiety selected from the group consisting of NH, O, SO, $SO_2$, (C=O), and S, and preferably NH, O, or S, optionally containing one to four additional heteroatoms in each ring. In some embodiments, the heterocyclyl contains between 1 and 3 or between 1 and 2 additional heteroatoms. Unless otherwise specified, a heterocyclyl may be saturated, partially unsaturated, aromatic or partially aromatic. The heterocyclyl group may be attached at any heteroatom or carbon atom that results in the creation of a stable structure.

Exemplary monocyclic heterocyclic groups can include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazaolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, hexahydroazepinyl, 4-piperidinyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dixolane and tetrahydro-1,1-dioxothienyl, dioxanyl, isothiazolidinyl, thietanyl, thiiranyl, triazinyl, triazolyl, tetrazolyl, azetidinyl and the like.

For example, where Q is a saturated 3-12 membered N-linked heterocyclyl, Q necessarily contains at least one nitrogen, and the carbon atoms are $sp^3$ hybridized. Where Q is a fused bicyclic heterocyclyl, the carbon atoms of the ring linked to L is $sp^3$ hybridized, provided the adjacent ring (and the common carbon atoms) may be $sp^2$, such as an indanyl where one of the carbon atoms has been replaced with nitrogen.

In general, exemplary bicyclic heterocyclyls include benzthiazolyl, benzoxazolyl, benzoxazinyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopridyl, furopyridinyl (such as furo{2,3-c}pyridinyl, furo{3,1-b}pyridinyl), or furo{2,3-b}pyridinyl), dihydroisoindolyl, dihydroquinazolinyl (such as 3,4-dihydro-4-oxo-quinazolinyl), tetrahydroquinolinyl (such as 1,2,3,4-tetrahydroquinolinyl), tetrahydroisoquinolinyl(such as 1,2,3,4-tetrahydroisoquiunolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isoindolyl, tetrahydroindoazolyl (such as 4,5,6,7-tetrahydroindoazolyl), isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl,

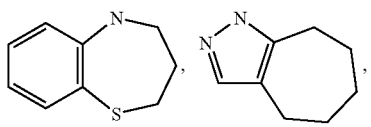

and the like.

Exemplary tricyclic heterocylclic groups include acridinyl, phenoxazinyl, phenazinyl, phenothiazinyl, carbozolyl, perminidinyl, phenanthrolinyl, carbolinyl, naphthothienyl, thianthrenyl, and the like.

Preferred heterocyclyl groups include morpholinyl, thiomorpholinyl, piperidinyl, piperazinyl, pyrrolidinyl, pyrimidinyl, pyridyl, pyrrolyl, imidazolyl, oxazolyl, isoxazolyl, acridinyl, azepinyl, hexahydroazepinyl, azetidinyl, indolyl, isoindolyl, thiazolyl, thiadiazolyl, quinolinyl, isoquinolinyl, 1,2,3,4-tetrahydroquinolinyl, 1,3,4-trihydroisoquinolinyl, 4,5,6,7-tetrahydroindadolyl, benzoxazinyl, benzoaxzolyl, benzthiazolyl, benzimidazolyl, tetrazolyl, oxadiazolyl,

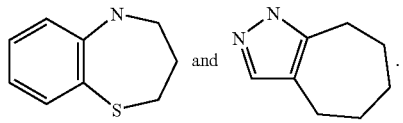

As used herein, unless otherwise noted, the term "heterocyclyl-alkyl" or "heterocyclyl-alkylene" shall denote any alkyl group substituted with a heterocyclyl group, wherein the heterocycly-alkyl group is bound through the alkyl portion to the central part of the molecule. Suitable examples of heterocyclyl-alkyl groups include, but are not limited to piperidinylmethyl, pyrrolidinylmethyl, piperidinylethyl, piperazinylmethyl, pyrrolylbutyl, piperidinylisobutyl, pyridylmethyl, pyrimidylethyl, and the like.

When a particular group is "substituted" (e.g., alkyl, alkylene, cycloalkyl, aryl, heterocyclyl, heteroaryl), that group may have one or more substituents, preferably from one to five substituents, more preferably from one to three substituents, most preferably from one to two substituents, independently selected from the list of substituents.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Under standard nomenclature used throughout this disclosure, the terminal portion of the designated side chain is described first, followed by the adjacent functionality toward the point of attachment. Thus, for example, a "phenyl(alkyl)amido(alkyl)" substituent refers to a group of the formula

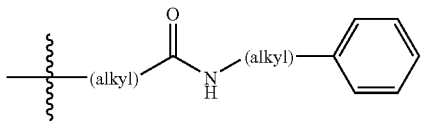

Unless otherwise noted, the position on the core phenyl ring of the compounds of formula (I) to which the $R^2$, $R^3$ and —$(CH_2)_m$-Q substituent groups are bound shall be defined as numbered in a clockwise direction around the phenyl ring, beginning with the carbon atom to which the —C(O)— group is bound, as drawn below

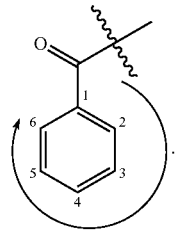

In the compounds of formula (I) of the present invention, $R^2$, $R^3$ and —$(CH_2)_m$-Q may be bound at the 2-, 3- and/or 4-positions only. Further, the 5- and 6-positions are unsubstituted. Thus, in the compounds of formula (I), the positions to which $R^2$, $R^3$ and —$(CH_2)_m$-Q are bound may be as listed below:

| 2-position | 3-position | 4-position |
| --- | --- | --- |
| $R^2$ | $R^3$ | —$(CH_2)_m$-Q |
| $R^3$ | $R^2$ | —$(CH_2)_m$-Q |
| $R^2$ | —$(CH_2)_m$-Q | $R^3$ |
| $R^3$ | —$(CH_2)_m$-Q | $R^2$ |
| —$(CH_2)_m$-Q | $R^2$ | $R^3$ |
| —$(CH_2)_m$-Q | $R^3$ | $R^2$ |

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes prevention, inhibition of onset, or alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Abbreviations used in the specification, particularly in the Schemes and Examples, are as follows:
CDI=N,N'-Carbonyldiimidazole
DCM=Dichloromethane
DIPEA=Diisopropyl ethyl amine
DMF=Dimethylformamide
DSC Differential Scanning Calorimetry
DVS=Dynamic Vapour Sorption
EDCI=1-(3-Dimethylaminopropyl)-3-ethylcarbodiimide hydrochloride
$Et_2O$=Diethyl Ether
EtOAc=Ethyl Acetate
EtOH=Ethanol
HOBt=1-Hydroxybenzotriazole
HPLC=High Performance Liquid Chromatography
MeOH=Methanol
MTBE=Methyl t-Butyl Ether NaBH(OAc)$_3$=Sodium triacetoxyborohydride
NMR=Nuclear Magnetic Resonance
OBt=—O-(1-benzotriazolyl)
RH=Relative Humidity
TEA or Et$_3$N=Triethylamine
THF=Tetrahydrofuran
TLC=Thin Layer Chromatography
XRD X-Ray Diffraction To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "leaving group" shall mean a charged or uncharged atom or group which departs during a substitution or displacement reaction. Suitable examples include, but are not limited to, Br, Cl, imidazolyl, and the like.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art. For example, one skilled in the art will recognize that in the processes of the present invention, it may be necessary and/or desirable to protect substituent groups such as (C$_{1-8}$ alkylcarbonyl)C$_{1-8}$alkyl.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

In an embodiment, the present invention is directed to processes for the preparation of compounds of formula (I) wherein $R^1$ is selected from the group consisting of $C_{1-6}$ alkyl (preferably isopropyl) and $C_{3-8}$ cycloalkyl (preferably cyclopropyl or cyclobutyl); n is 1; $R^2$ and $R^3$ are each hydrogen; $R^4$ is —$(CH_2)$-Q; and Q is a 5- to 6-membered N-linked heterocyclyl, wherein in addition to N-linking nitrogen, the heterocyclyl may optionally contain between 1 and 2 additional heteroatoms independently selected form O, S and NH.

In an embodiment, the present invention is directed to processes for the preparation of compounds of formula (I) wherein:
(a) n is 1;
(b) $R^1$ is $C_{1-10}$ alkyl (preferably branched);
(c) $R^1$ is branched $C_{3-5}$ alkyl;
(d) one of $R^2$, $R^3$ and $R^4$ is G; (preferably one of $R^3$ and $R^4$ is G)
(e) $R^4$ is G;
(f) L is unbranched —$(CH_2)_m$—, wherein m is an integer from 1 to 4;
(g) L is —$CH_2$—;
(h) Q is a saturated N-linked nitrogen-containing heterocyclyl;
(i) Q is substituted or unsubstituted piperidinyl, diazepanyl, azepanyl, decahydroisoquinolin-2-yl, piperazinyl, pyrrolinyl, pyrrolidinyl, thiomorpholinyl, or morpholinyl;
(j) Q is unsubstituted diazepanyl, azepanyl, morpholinyl, decahydroisoquinolin-2-yl, piperidinyl, or pyrrolidinyl;
(k) substituted Q are selected from N-($C_{1-6}$ alkyl)piperazinyl, N-phenyl-piperazinyl, 1,3,8-triaza-spiro{4.5}decyl, and 1,4-dioxa-8-aza-spiro{4.5}decyl;
(l) Q is a monovalent radical of an amine selected from aziridine, 1,4,7-trioxa-10-aza-cyclododecane, thiazolidine, 1-phenyl-1,3,8-triaza-spiro{4.5}decan-4-one, piperidine-3-carboxylic acid diethylamide, 1,2,3,4,5,6-hexahydro-{2,3'}bipyridinyl, 4-(3-trifluoromethyl-phenyl)-piperazine, 2-piperazin-1-yl-pyrimidine, piperidine-4-carboxylic acid amide, methyl-(2-pyridin-2-yl-ethyl)-amine, {2-(3,4-dimethoxy-phenyl)-ethyl}-methyl-amine, thiomorpholinyl, allyl-cyclopentyl-amine, {2-(1H-indol-3-yl)-ethyl}-methyl-amine, 1-piperidin-4-yl-1,3-dihydro-benzoimidazol-2-one, 2-(piperidin-4-yloxy)-pyrimidine, piperidin-4-yl-pyridin-2-yl-amine, phenylamine, and pyridin-2-ylamine;

(m) Q is selected from diazepanyl, azepanyl, morpholinyl, piperidinyl, and pyrrolidinyl, optionally substituted with between 1 and 3 substituents independently selected from hydroxy, halo, carboxamide, $C_{1-6}$ alkyl, 5-9 membered or 6-9 membered heterocyclyl, —N($C_{1-6}$ alkyl)(5-9 membered or 6-9 membered heterocyclyl), —NH(5-9 membered or 6-9 membered heterocyclyl), —O(5-9 or 6-9 membered heterocyclyl), (5-9 membered or 6-9 membered heterocyclyl)$C_{1-3}$ alkylene, $C_{1-6}$ alkoxy, ($C_{3-6}$ cycloalkyl)—O—, phenyl, (phenyl)$C_{1-3}$ alkylene, and (phenyl)$C_{1-3}$ alkylene—O—, where each of above heterocyclyl, phenyl, and alkyl groups may be optionally substituted with from 1 to 3 substituents independently selected from trifluoromethyl, methoxy, halo, nitro, cyano, hydroxy, and $C_{1-3}$ alkyl;

(n) Q is substituted with a substituent comprising a 5-9 membered or 6-9 membered heterocyclyl group selected from: pyridyl, pyrimidyl, furyl, thiofuryl, imidazolyl, (imidazolyl)$C_{1-6}$ alkylene, oxazolyl, thiazolyl, 2,3-dihydro-indolyl, benzimidazolyl, 2-oxobenzimidazolyl, (tetrazolyl)$C_{1-6}$ alkylene, tetrazolyl, (triazolyl)$C_{1-6}$ alkylene, triazolyl, (pyrrolyl) $C_{1-6}$ alkylene, pyrrolidinyl, and pyrrolyl;
(o) Q is piperidinyl;
(p) $R^8$ is hydrogen;
(q) $R^9$ is $C_{1-6}$ alkyl;
(r) $R^9$ is unsubstituted or substituted phenyl;
(s) $R^8$ and $R^9$ independently are $C_{1-6}$ alkyl;
(t) $R^8$ and $R^9$ are methyl;
(u) $R^8$ and $R^9$ are ethyl;
(v) $R^9$ is selected from phenyl or 5-9 membered aromatic heterocyclyl, wherein said phenyl or aromatic heterocyclyl is optionally substituted with 1-3 substituents selected from methoxy, hydroxy, halo, nitro, cyano, trifluoromethyl, and $C_{1-3}$ alkyl;
(w) $R^9$ is selected from substituted or unsubstituted phenyl, pyridyl, pyrimidyl, furyl, thiofuryl, imidazolyl, (imidazolyl) $C_{1-6}$ alkylene, oxazolyl, thiazolyl, 2,3-dihydro-indolyl, benzimidazolyl, 2-oxobenzimidazolyl, (tetrazolyl)$C_{1-6}$ alkylene, tetrazolyl, (triazolyl)$C_{1-6}$ alkylene, triazolyl, (pyrrolyl)$C_{1-6}$ alkylene, pyrrolidinyl, and pyrrolyl;
(x) $R^9$ is substituted or unsubstituted pyridyl;
(y) X is O; and
(z) combinations of (a) through (z) above.

In another embodiment, the present invention is directed to processes for the preparation of compounds of formula (I) selected from the group consisting of:
(4-{[Ethyl-(2-methoxy-ethyl)-amino]-methyl}-phenyl)-(4-isopropyl-piperazin-1-yl)-methanone;
(4-Azepan-1-ylmethyl-phenyl)-(4-isopropyl-piperazin-1-yl)-methanone dihydrochloride;
(4-Azepan-1-ylmethyl-phenyl)-(4-sec-butyl-piperazin-1-yl)-methanone;
(4-Azepan-1-yl methyl-phenyl)-{4-(1-ethyl-propyl)-piperazin-1-yl}-methanone;
(4-Butyl-piperazin-1-yl)-(4-dimethylaminomethyl-phenyl)-methanone;
(4-Butyl-piperazin-1-yl)-(4-morpholin-4-ylmethyl-phenyl)-methanone;
(4-Butyl-piperazin-1-yl)-{4-(3-trifluoromethyl-piperidin-1-ylmethyl)-phenyl}-methanone;
(4-Butyl-piperazin-1-yl)-{4-{(4-trifluoromethyl-phenylamino)-methyl}-phenyl}-methanone;

(4-Cyclohexyl-piperazin-1-yl)-(4-piperidin-1-ylmethyl-phenyl)-methanone;
(4-Diethylaminomethyl-phenyl)-(4-isopropyl-piperazin-1-yl)-methanone dihydrochloride;
(4-Dimethylaminomethyl-phenyl)-(4-isopropyl-piperazin-1-yl)-methanone dihydrochloride;
(4-Dimethylaminomethyl-phenyl)-{4-(1-ethyl-propyl)-piperazin-1-yl}-methanone dihydrochloride;
(4-Isopropyl-piperazin-1-yl)-(3-morpholin-4-ylmethyl-phenyl)-methanone;
(4-Isopropyl-piperazin-1-yl)-(3-piperidin-1-ylmethyl-phenyl)-methanone;
(4-Isopropyl-piperazin-1-yl)-(4-{[(2-methoxy-ethyl)-propyl-amino]-methyl}-phenyl)-methanone;
(4-Isopropyl-piperazin-1-yl)-(4-morpholin-4-ylmethyl-phenyl)-methanone;
(4-Isopropyl-piperazin-1-yl)-(4-phenylaminomethyl-phenyl)-methanone dihydrochloride;
(4-Isopropyl-piperazin-1-yl)-(4-piperidin-1-ylmethyl-phenyl)-methanone;
(4-Isopropyl-piperazin-1-yl)-(4-pyrrolidin-1-ylmethyl-phenyl)-methanone dihydrochloride;
(4-Isopropyl-piperazin-1-yl)-(4-thiomorpholin-4-ylmethyl-phenyl)-methanone;
(4-Isopropyl-piperazin-1-yl)-{4-(3-trifluoromethyl-piperidin-1-ylmethyl)-phenyl}-methanone dihydrochloride;
(4-Isopropyl-piperazin-1-yl)-{4-(4-isopropyl-piperazin-1-ylmethyl)-phenyl}-methanone;
(4-Isopropyl-piperazin-1-yl)-{4-[(2-methoxy-ethylamino)-methyl]-phenyl}-methanone;
(4-Isopropyl-piperazin-1-yl)-[4-(pyridin-2-ylaminomethyl)-phenyl]-methanone;
(4-Isopropyl-piperazin-1-yl)-{4-[(2-methoxy-1-methyl-ethylamino)-methyl]-phenyl}-methanone;
(4-Isopropyl-piperazin-1-yl)-{4-{(4-trifluoromethyl-phenylamino)-methyl}-phenyl}-methanone;
(4-Isopropyl-piperazin-1-yl)-{4-{(4-trifluoromethyl-pyridin-2-ylamino)-methyl}-phenyl}-methanone dihydrochloride;
(4-Isopropyl-piperazin-1-yl)-{4-{(5-trifluoromethyl-pyridin-2-ylamino)-methyl}-phenyl}-methanone dihydrochloride;
(4-Isopropyl-piperazin-1-yl)-{4-{(6-trifluoromethyl-pyridin-3-ylamino)-methyl}-phenyl}-methanone dihydrochloride;
(4-Methyl-piperazin-1-yl)-(4-morpholin-4-ylmethyl-phenyl)-methanone dihydrochloride;
(4-Methyl-piperazin-1-yl)-(4-piperidin-1-ylmethyl-phenyl)-methanone dihydrochloride;
(4-sec-Butyl-piperazin-1-yl)-(4-dimethylaminomethyl-phenyl)-methanone;
(4-sec-Butyl-piperazin-1-yl)-(4-morpholin-4-ylmethyl-phenyl)-methanone dihydrochloride;
(4-sec-Butyl-piperazin-1-yl)-(4-phenylaminomethyl-phenyl)-methanone;
(4-sec-Butyl-piperazin-1-yl)-(4-piperidin-1-ylmethyl-phenyl)-methanone;
(4-sec-Butyl-piperazin-1-yl)-(4-pyrrolidin-1-ylmethyl-phenyl)-methanone;
(4-sec-Butyl-piperazin-1-yl)-{4-(3-trifluoromethyl-piperidin-1-ylmethyl)-phenyl}-methanone dihydrochloride;
{3-(4-Benzyl-piperidin-1-ylmethyl)-phenyl}-(4-methyl-piperazin-1-yl)-methanone;
{4-(1-Ethyl-propyl)-piperazin-1-yl}-(4-morpholin-4-ylmethyl-phenyl)-methanone dihydrochloride;
{4-(1-Ethyl-propyl)-piperazin-1-yl}-(4-phenylaminomethyl-phenyl)-methanone dihydrochloride;
{4-(1-Ethyl-propyl)-piperazin-1-yl}-(4-piperidin-1-ylmethyl-phenyl)-methanone;
{4-(1-Ethyl-propyl)-piperazin-1-yl}-(4-pyrrolidin-1-ylmethyl-phenyl)-methanone;
{4-(1-Ethyl-propyl)-piperazin-1-yl}-{4-(3-trifluoromethyl-piperidin-1-yl methyl)-phenyl}-methanone dihydrochloride;
{4-(1-Ethyl-propyl)-piperazin-1-yl}-{4-(decahydro-isoquinolin-2-ylmethyl)-phenyl}-methanone;
{4-(1-Ethyl-propyl)-piperazin-1-yl}-{4-{(4-trifluoromethyl-phenylamino)-methyl}-phenyl}-methanone dihydrochloride;
{4-(1-Methyl-heptyl)-piperazin-1-yl}-(4-morpholin-4-ylmethyl-phenyl)-methanone;
{4-(1-Methyl-heptyl)-piperazin-1-yl}-(4-piperidin-1-ylmethyl-phenyl)-methanone;
{4-(Benzylamino-methyl)-phenyl}-(4-isopropyl-piperazin-1-yl)-methanone dihydrochloride;
{4-(Benzylamino-methyl)-phenyl}-{4-(1-ethyl-propyl)-piperazin-1-yl}-methanone; and
{4-{(5-Chloro-pyridin-2-ylamino)-methyl}-phenyl}-(4-isopropyl-piperazin-1-yl)-methanone dihydrochloride.

Preferably, the processes of the present invention are directed to making compounds selected from the group consisting of:

(4-{[Ethyl-(2-methoxy-ethyl)-amino]-methyl}-phenyl)-(4-isopropyl-piperazin-1-yl)-methanone;
(4-Azepan-1-ylmethyl-phenyl)-(4-isopropyl-piperazin-1-yl)-methanone dihydrochloride;
(4-Azepan-1-ylmethyl-phenyl)-(4-sec-butyl-piperazin-1-yl)-methanone;
(4-Azepan-1-yl methyl-phenyl)-{4-(1-ethyl-propyl)-piperazin-1-yl}-methanone;
(4-Butyl-piperazin-1-yl)-(4-dimethylaminomethyl-phenyl)-methanone;
(4-Butyl-piperazin-1-yl)-(4-morpholin-4-ylmethyl-phenyl)-methanone;
(4-Butyl-piperazin-1-yl)-{4-(3-trifluoromethyl-piperidin-1-ylmethyl)-phenyl}-methanone;
(4-Cyclohexyl-piperazin-1-yl)-(4-piperidin-1-ylmethyl-phenyl)-methanone;
(4-Diethylaminomethyl-phenyl)-(4-isopropyl-piperazin-1-yl)-methanone dihydrochloride;
(4-Dimethylaminomethyl-phenyl)-(4-isopropyl-piperazin-1-yl)-methanone dihydrochloride;
(4-Dimethylaminomethyl-phenyl)-{4-(1-ethyl-propyl)-piperazin-1-yl}-methanone dihydrochloride;
(4-Isopropyl-piperazin-1-yl)-(3-piperidin-1-ylmethyl-phenyl)-methanone;
(4-Isopropyl-piperazin-1-yl)-(4-{[(2-methoxy-ethyl)-propyl-amino]-methyl}-phenyl)-methanone;
(4-Isopropyl-piperazin-1-yl)-(4-morpholin-4-ylmethyl-phenyl)-methanone;
(4-Isopropyl-piperazin-1-yl)-(4-phenylaminomethyl-phenyl)-methanone dihydrochloride;
(4-Isopropyl-piperazin-1-yl)-(4-piperidin-1-ylmethyl-phenyl)-methanone;
(4-Isopropyl-piperazin-1-yl)-(4-pyrrolidin-1-ylmethyl-phenyl)-methanone dihydrochloride;
(4-Isopropyl-piperazin-1-yl)-(4-thiomorpholin-4-ylmethyl-phenyl)-methanone;
(4-Isopropyl-piperazin-1-yl)-{4-(3-trifluoromethyl-piperidin-1-ylmethyl)-phenyl}-methanone dihydrochloride;
(4-Isopropyl-piperazin-1-yl)-{4-(4-isopropyl-piperazin-1-ylmethyl)-phenyl}-methanone;
(4-Isopropyl-piperazin-1-yl)-{4-[(2-methoxy-ethylamino)-methyl]-phenyl}-methanone;

(4-Isopropyl-piperazin-1-yl)-[4-(pyridin-2-ylaminomethyl)-phenyl]-methanone;
(4-Isopropyl-piperazin-1-yl)-{4-[(2-methoxy-1-methyl-ethylamino)-methyl]-phenyl}-methanone;
(4-Isopropyl-piperazin-1-yl)-{4-{(5-trifluoromethyl-pyridin-2-ylamino)-methyl}-phenyl}-methanone dihydrochloride;
(4-Isopropyl-piperazin-1-yl)-{4-{(6-trifluoromethyl-pyridin-3-ylamino)-methyl}-phenyl}-methanone dihydrochloride;
(4-Methyl-piperazin-1-yl)-(4-morpholin-4-ylmethyl-phenyl)-methanone dihydrochloride;
(4-Methyl-piperazin-1-yl)-(4-piperidin-1-ylmethyl-phenyl)-methanone dihydrochloride;
(4-sec-Butyl-piperazin-1-yl)-(4-dimethylaminomethyl-phenyl)-methanone;
(4-sec-Butyl-piperazin-1-yl)-(4-morpholin-4-ylmethyl-phenyl)-methanone dihydrochloride;
(4-sec-Butyl-piperazin-1-yl)-(4-phenylaminomethyl-phenyl)-methanone;
(4-sec-Butyl-piperazin-1-yl)-(4-piperidin-1-ylmethyl-phenyl)-methanone;
(4-sec-Butyl-piperazin-1-yl)-(4-pyrrolidin-1-ylmethyl-phenyl)-methanone;
(4-sec-Butyl-piperazin-1-yl)-{4-(3-trifluoromethyl-piperidin-1-ylmethyl)-phenyl}-methanone dihydrochloride;
{4-(1-Ethyl-propyl)-piperazin-1-yl}-(4-morpholin-4-ylmethyl-phenyl)-methanone dihydrochloride;
{4-(1-Ethyl-propyl)-piperazin-1-yl}-(4-piperidin-1-ylmethyl-phenyl)-methanone;
{4-(1-Ethyl-propyl)-piperazin-1-yl}-(4-pyrrolidin-1-ylmethyl-phenyl)-methanone;
{4-(1-Ethyl-propyl)-piperazin-1-yl}-{4-(3-trifluoromethyl-piperidin-1-yl methyl) -phenyl}-methanone dihydrochloride;
{4-(1-Ethyl-propyl)-piperazin-1-yl}-{4-(decahydro-isoquinolin-2-ylmethyl)-phenyl}-methanone;
{4-(Benzylamino-methyl)-phenyl}-(4-isopropyl-piperazin-1-yl)-methanone dihydrochloride;
{4-(Benzylamino-methyl)-phenyl}-{4-(1-ethyl-propyl)-piperazin-1-yl}-methanone; and
{4-{(5-Chloro-pyridin-2-ylamino)-methyl}-phenyl}-(4-isopropyl-piperazin-1-yl)-methanone dihydrochloride.

Preferably, the present invention is directed to processes for the preparation of a compound of formula (I) selected from the group consisting of:
(4-{[Ethyl-(2-methoxy-ethyl)-amino]-methyl}-phenyl)-(4-isopropyl-piperazin-1-yl)-methanone;
(4-Azepan-1-ylmethyl-phenyl)-(4-isopropyl-piperazin-1-yl)-methanone dihydrochloride;
(4-Azepan-1-ylmethyl-phenyl)-(4-sec-butyl-piperazin-1-yl)-methanone;
(4-Azepan-1-yl methyl-phenyl)-{4-(1-ethyl-propyl)-piperazin-1-yl}-methanone;
(4-Butyl-piperazin-1-yl)-(4-morpholin-4-ylmethyl-phenyl)-methanone;
(4-Cyclohexyl-piperazin-1-yl)-(4-piperidin-1-ylmethyl-phenyl)-methanone;
(4-Diethylaminomethyl-phenyl)-(4-isopropyl-piperazin-1-yl)-methanone dihydrochloride;
(4-Dimethylaminomethyl-phenyl)-(4-isopropyl-piperazin-1-yl)-methanone dihydrochloride;
(4-Dimethylaminomethyl-phenyl)-{4-(1-ethyl-propyl)-piperazin-1-yl}-methanone dihydrochloride;
(4-Isopropyl-piperazin-1-yl)-(4-{[(2-methoxy-ethyl)-propyl-amino]-methyl}-phenyl)-methanone;
(4-Isopropyl-piperazin-1-yl)-(4-morpholin-4-ylmethyl-phenyl)-methanone;
(4-Isopropyl-piperazin-1-yl)-(4-piperidin-1-ylmethyl-phenyl)-methanone;
(4-Isopropyl-piperazin-1-yl)-(4-pyrrolidin-1-ylmethyl-phenyl)-methanone dihydrochloride;
(4-Isopropyl-piperazin-1-yl)-(4-thiomorpholin-4-ylmethyl-phenyl)-methanone;
(4-Isopropyl-piperazin-1-yl)-{4-(3-trifluoromethyl-piperidin-1-ylmethyl)-phenyl}-methanone dihydrochloride;
(4-Isopropyl-piperazin-1-yl)-{4-[(2-methoxy-ethylamino)-methyl]-phenyl}-methanone;
(4-Isopropyl-piperazin-1-yl)-[4-(pyridin-2-ylaminomethyl)-phenyl]-methanone;
(4-Isopropyl-piperazin-1-yl)-{4-[(2-methoxy-1-methyl-ethylamino)-methyl]-phenyl}-methanone;
(4-sec-Butyl-piperazin-1-yl)-(4-dimethylaminomethyl-phenyl)-methanone;
(4-sec-Butyl-piperazin-1-yl)-(4-morpholin-4-ylmethyl-phenyl)-methanone dihydrochloride;
(4-sec-Butyl-piperazin-1-yl)-(4-piperidin-1-ylmethyl-phenyl)-methanone;
(4-sec-Butyl-piperazin-1-yl)-(4-pyrrolidin-1-ylmethyl-phenyl)-methanone;
{4-(1-Ethyl-propyl)-piperazin-1-yl}-(4-morpholin-4-ylmethyl-phenyl)-methanone dihydrochloride;
{4-(1-Ethyl-propyl)-piperazin-1-yl}-(4-piperidin-1-ylmethyl-phenyl)-methanone;
{4-(1-Ethyl-propyl)-piperazin-1-yl}-(4-pyrrolidin-1-ylmethyl-phenyl)-methanone;
{4-(1-Ethyl-propyl)-piperazin-1-yl}-{4-(3-trifluoromethyl-piperidin-1-yl methyl)-phenyl}-methanone dihydrochloride;
{4-(1-Ethyl-propyl)-piperazin-1-yl}-{4-(decahydro-isoquinolin-2-ylmethyl)-phenyl}-methanone;
{4-(Benzylamino-methyl)-phenyl}-(4-isopropyl-piperazin-1-yl)-methanone dihydrochloride; and
{4-(Benzylamino-methyl)-phenyl}-{4-(1-ethyl-propyl)-piperazin-1-yl}-methanone.

More preferably, the present invention is directed to processes for the preparation of a compound of formula (I) selected from the group consisting of:
(4-Azepan-1-ylmethyl-phenyl)-(4-isopropyl-piperazin-1-yl)-methanone dihydrochloride;
(4-Azepan-1-ylmethyl-phenyl)-(4-sec-butyl-piperazin-1-yl)-methanone;
(4-Cyclohexyl-piperazin-1-yl)-(4-piperidin-1-ylmethyl-phenyl)-methanone;
(4-Isopropyl-piperazin-1-yl)-(4-piperidin-1-ylmethyl-phenyl)-methanone;
(4-Isopropyl-piperazin-1-yl)-(4-pyrrolidin-1-ylmethyl-phenyl)-methanone dihydrochloride;
(4-Isopropyl-piperazin-1-yl)-{4-(3-trifluoromethyl-piperidin-1-ylmethyl)-phenyl}-methanone dihydrochloride;
(4-sec-Butyl-piperazin-1-yl)-(4-dimethylaminomethyl-phenyl)-methanone;
(4-sec-Butyl-piperazin-1-yl)-(4-piperidin-1-ylmethyl-phenyl)-methanone;
(4-sec-Butyl-piperazin-1-yl)-(4-pyrrolidin-1-ylmethyl-phenyl)-methanone;

{4-(1-Ethyl-propyl)-piperazin-1-yl}-(4-morpholin-4-ylm-ethyl-phenyl)-methanone dihydrochloride;

{4-(1-Ethyl-propyl)-piperazin-1-yl}-(4-piperidin-1-ylm-ethyl-phenyl)-methanone; and {4-(1-Ethyl-propyl)-piperazin-1-yl}-(4-pyrrolidin-1-ylm-ethyl-phenyl)-methanone.

More preferably still, the present invention is directed to processes for the preparation of a compound of formula (I) selected from the group consisting of:

(4-Azepan-1-ylmethyl-phenyl)-(4-sec-butyl-piperazin-1-yl)-methanone;

(4-Isopropyl-piperazin-1-yl)-(4-piperidin-1-ylmethyl-phenyl)-methanone;

(4-sec-Butyl-piperazin-1-yl)-(4-piperidin-1-ylmethyl-phenyl)-methanone;

{4-(1-Ethyl-propyl)-piperazin-1-yl}-(4-piperidin-1-ylm-ethyl-phenyl)-methanone;

{4-(1-Ethyl-propyl)-piperazin-1-yl}-(4-pyrrolidin-1-ylm-ethyl-phenyl)-methanone;

(4-Isopropyl-piperazin-1-yl)-(4-morpholin-4-ylmethyl-phenyl)-methanone;

(4-sec-Butyl-piperazin-1-yl)-(4-morpholin-4-ylmethyl-phenyl)-methanone dihydrochloride; and {4-(1-Ethyl-propyl)-piperazin-1-yl}-(4-morpholin-4-ylm-ethyl-phenyl)-methanone dihydrochloride.

The present invention is directed to a process for the preparation of compounds of formula (I). The process of the present invention is advantageous for large scale and/or commercial purposes because it does not require isolation and/or purification of oily intermediates; and does not require column chromatography which is impractical and highly cost prohibitive on a large and/or commercial scale. Additionally, the process of the present invention may be completed in a single solvent system, whereas the process as disclosed in US Patent Application Publication 2004-0010746 A1, published Apr. 21, 2005 (also published as PCT Publication WO 2004/037801, May 6, 2004) requires multiple solvents (including reaction and extractive work-up solvents).

The present invention is directed to a process for the preparation of compounds of formula (I), as described in more detail in Scheme 1 below.

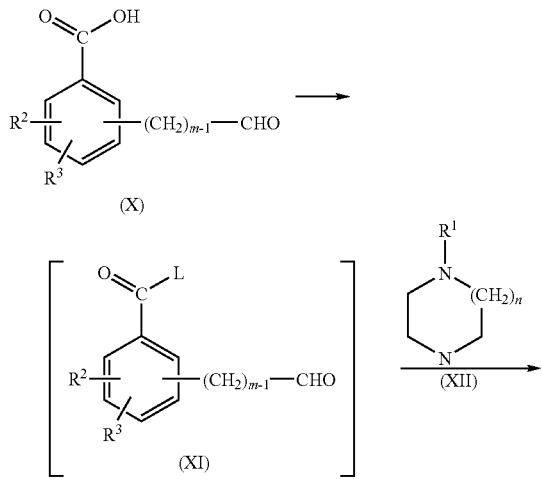

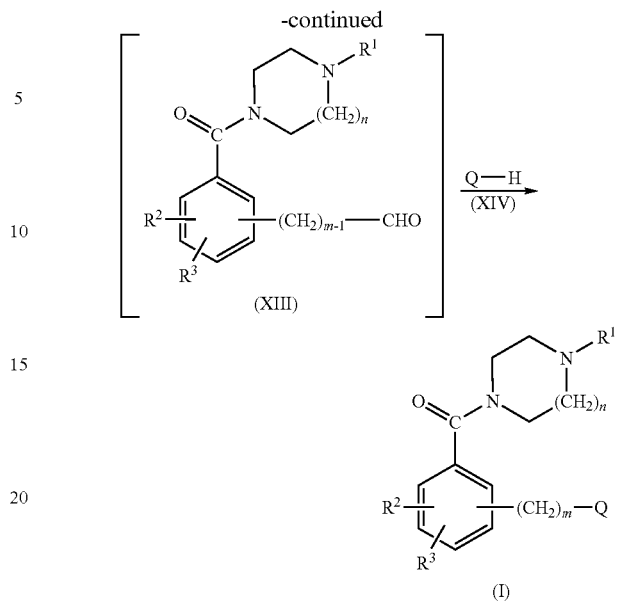

Accordingly, a suitably substituted compound of formula (X), a known compound or compound prepared by known methods, is activated according to known methods, in a first organic solvent; to yield the corresponding compound of formula (XI), wherein L is a suitable leaving group such as chloro, bromo, —OC(O)O—$C_{1-4}$alkyl, OBt (wherein the activating agent is HOBt), -imidazolide (wherein the activating agent is CDI), and the like; preferably chloro.

For example, wherein L is chloro, the compound of formula (X) is reacted with a suitable chlorinating agent such as oxalyl chloride, thionyl chloride, phosphorus oxychloride, and the like, preferably about 1.05 equivalents of oxalyl chloride in the presence of a catalytic amount of DMF; in an organic solvent such as THF, toluene, dichloromethane, dichloroethane, acetonitrile, and the like, preferably THF. Alternatively, the compound of formula (X) is reacted with Vilsmeier's reagent (chloromethylene-dimethyl-ammonium chloride) in an organic solvent such as DCM; at a temperature in the range of from about 0° C. to about room temperature.

The compound of formula (XI) is not isolated.

The compound of formula (XI) is reacted with a suitably substituted compound of formula (XII), a known compound or compound prepared by known methods, wherein the compound of formula (XII) is preferably present in an amount equal to about one equivalent, more preferably about 0.95 equivalents; in the presence of an organic or inorganic base (solid or aqueous) such as TEA, DIPEA, pyridine, NaOH, KOH, sodium carbonate, potassium carbonate, and the like, preferably 50% aqueous NaOH; wherein the base is organic, preferably in the absence of water; in a second organic solvent such as THF, toluene, acetonitrile, and the like, preferably THF; to yield the corresponding compound of formula (XIII).

The compound of formula (XIII) is not isolated.

The compound of formula (XIII) is reacted with a suitably substituted compound of formula (XIV), a known compound or compound prepared by known methods, wherein the compound of formula (XIV) is preferably present in an amount greater than about one equivalent, more preferably in an amount in the range of from about 1 to about 5 equivalents, more preferably still in an amount in the range of from about 1.5 to about 2.5 equivalents, most preferably in an amount in the range of from about 1.5 to about 2 equivalents; in the presence of a reducing agent such as NaBH(OAc)$_3$, NaBH$_4$, sodium cyanoborohydride, and the like, preferably, NaBH(OAc)$_3$; wherein the reducing agent is preferably present in an amount in the range of from about 1 to about 2 equivalents, more preferably in an amount in the range of from about 1.25 to about 1.5 equivalents; in a third organic solvent such as THF, toluene, acetonitrile, and the like, preferably, THF; to yield the corresponding compound of formula (I).

Preferably, the compound of formula (I) is not isolated and/or purified. More preferably, the compound of formula (I) is reacted according to known methods, to yield a corresponding pharmaceutically acceptable salt of the compound of formula (I). Optionally, the compound of formula (I) is isolated and/or purified according to known methods.

Preferably, the first organic solvent, the second organic solvent and the third organic solvent are the same. Preferably, the conversion of the compound of formula (X) to the corresponding compound of formula (I) is completed in a single solvent system.

In an embodiment of the present invention, the compound of formula (I) is further reacted with a suitably selected pharmaceutically acceptable acid to yield the corresponding pharmaceutically acceptable salt of the compound of formula (I). In an embodiment of the present invention, the compound of formula (I) is not isolated and is reacted with a suitably selected pharmaceutically acceptable acid to yield the corresponding pharmaceutically acceptable salt of the compound of formula (I).

One skilled in the art will recognize that in the synthesis of compounds of formula (I) wherein the —(CH$_2$)$_m$-Q substituent group is bound to the 2-position on the phenyl ring, the aldehyde on the compound of formula (X) is preferably protected, with a suitable protecting groups according to known methods, until after the reaction with the compound of formula (XII) and then de-protected to react with the compound of formula (XIV).

In an embodiment, the present invention is directed to a process for the preparation of the compound of formula (Is), also known as (4-isopropyl-piperazin-1-yl)-(4-morpholin-4-ylmethyl-phenyl)-methanone, as described in more detail in Scheme 2 below.

Scheme 2

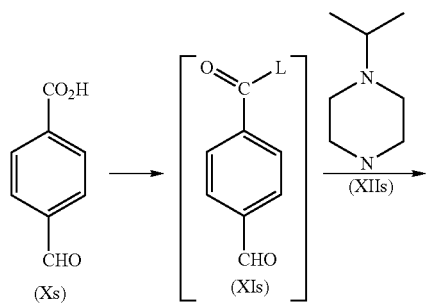

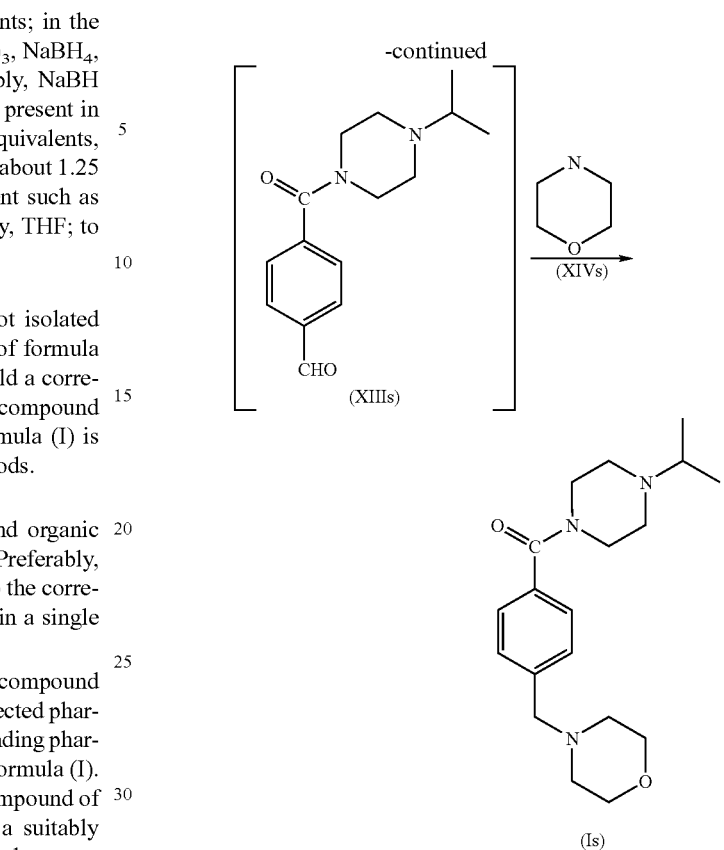

Accordingly, a suitably substituted compound of formula (Xs), also known as 4-formyl-benzoic acid, a known compound, is activated according to known methods, in a first organic solvent, to yield the corresponding compound of formula (XIs), wherein L is a suitable leaving group such as chloro, bromo, —OC(O)O—C$_{1-4}$alkyl, OBt (wherein the activating agent is HOBt), -imidazolide (wherein the activating agent is CDI), and the like; preferably chloro.

For example, wherein L is chloro, the compound of formula (Xs) is reacted with a suitable chlorinating agent such as oxalyl chloride, thionyl chloride, phosphorus oxychloride, and the like, preferably about 1.05 equivalents of oxalyl chloride in the presence of a catalytic amount of DMF; in an organic solvent such as THF, toluene, dichloromethane, dichloroethane, acetonitrile, and the like, preferably THF. Alternatively, the compound of formula (Xs) is reacted with Vilsmeier's reagent (chloromethylene-dimethyl-ammonium chloride) in an organic solvent such as DCM; at a temperature in the range of from about 0° C. to about room temperature.

The compound of formula (XIs) is not isolated.

The compound of formula (XIs) is reacted with a suitably substituted compound of formula (XIIs), also known as N-isopropylpiperazine, a known compound; wherein the compound of formula (XIIs) is preferably present in an amount equal to about one equivalent, more preferably about 0.95 equivalents; in the presence of an organic or inorganic base (solid or aqueous) such as TEA, DIPEA, pyridine, NaOH, KOH, sodium carbonate, potassium carbonate, and the like, preferably 50% aqueous NaOH; wherein the base is organic, preferably in the absence of water; in a second organic solvent such as THF, toluene, acetonitrile, and the like, preferably THF; to yield the corresponding compound of formula (XIIIs), also known as 4-(4-isopropyl-piperazine-1-carbonyl)-benzaldehyde.

The compound of formula (XIIIs) is not isolated.

The compound of formula (XIIIs) is reacted with a suitably substituted compound of formula (XIVs), also known as morpholine, a known compound, wherein the compound of formula (XIVs) is preferably present in an amount greater than about one equivalent, more preferably in an amount in the range of from about 1 to about 5 equivalents, more preferably still in an amount in the range of from about 1.5 to about 2.5 equivalents, most preferably in an amount in the range of from about 1.5 to about 2 equivalents; in the presence of a reducing agent such as $NaBH(OAc)_3$, $NaBH_4$, sodium cyanoborohydride, and the like, preferably, $NaBH(OAc)_3$; wherein the reducing agent is preferably present in an amount in the range of from about 1 to about 2 equivalents, more preferably in an amount in the range of from about 1.25 to about 1.5 equivalents; in a third organic solvent such as THF, toluene, acetonitrile, and the like, preferably, THF; to yield the corresponding compound of formula (Is), also known as (4-isopropyl-piperazin-1-yl)-(4-morpholin-4-ylmethyl-phenyl)-methanone.

Preferably, the compound of formula (Is) is not isolated and/or purified. More preferably, the compound of formula (Is) is reacted, according to known methods, to yield a corresponding pharmaceutically acceptable salt of the compound of formula (Is), more preferably still the mono-succinate salt of the compound of formula (Is). Optionally, the compound of formula (Is) is isolated and/or purified according to known methods.

In an embodiment of the present invention, the compound of formula (Is) is further reacted with a suitably selected pharmaceutically acceptable acid to yield the corresponding pharmaceutically acceptable salt of the compound of formula (Is). In an embodiment of the present invention, the compound of formula (Is) is not isolated and is reacted with a suitably selected pharmaceutically acceptable acid to yield the corresponding pharmaceutically acceptable salt of the compound of formula (Is).

US Patent Application Publication 2004-0010746 A1, published Apr. 21, 2005 (also published as PCT Publication WO 2004/037801, May 6, 2004) discloses a process for the preparation of the compounds of formula (I). In an embodiment, the present invention is directed to improvements in the process for the preparation of the compounds of formula (I) as disclosed in US Patent Application Publication 2004-0010746 A1.

More specifically, the improvements of the present invention are the preparation of a bisulfite intermediate (a compound of formula (XVII)) in the Schemes which follow herein) which may be isolated as a solid, thereby providing an improved means of purification (in the process disclosed in US Patent Application Publication 2004-0010746 A1 the aldehyde intermediate of formula (XIII) is isolated as an oil and then purified by column chromatography). Additionally, the bisulfite intermediate provides improved stability and shelf-life relative to the aldehyde intermediate.

In an embodiment, the present invention is directed to a process for the purification of the aldehyde intermediate, a compound of formula (XII), comprising preparation of its corresponding bisulfite derivative, isolation of said bisulfite derivative as a solid, by for example filtration, and optionally purification according to known methods, for example by recrystallization from a suitable solvent such as methanol, ethanol, isopropanol, acetonitrile, and the like, preferably ethanol. The bi-sulfite derivative may then be further reacted as described herein to yield the desired compound of formula (I) or alternatively, may be reacted to re-form the compound of formula (XIII), which is then reacted according to the processes as described herein, to yield the desired compound of formula (I).

The improved process of the present invention is as described in more detail in Scheme 3 below.

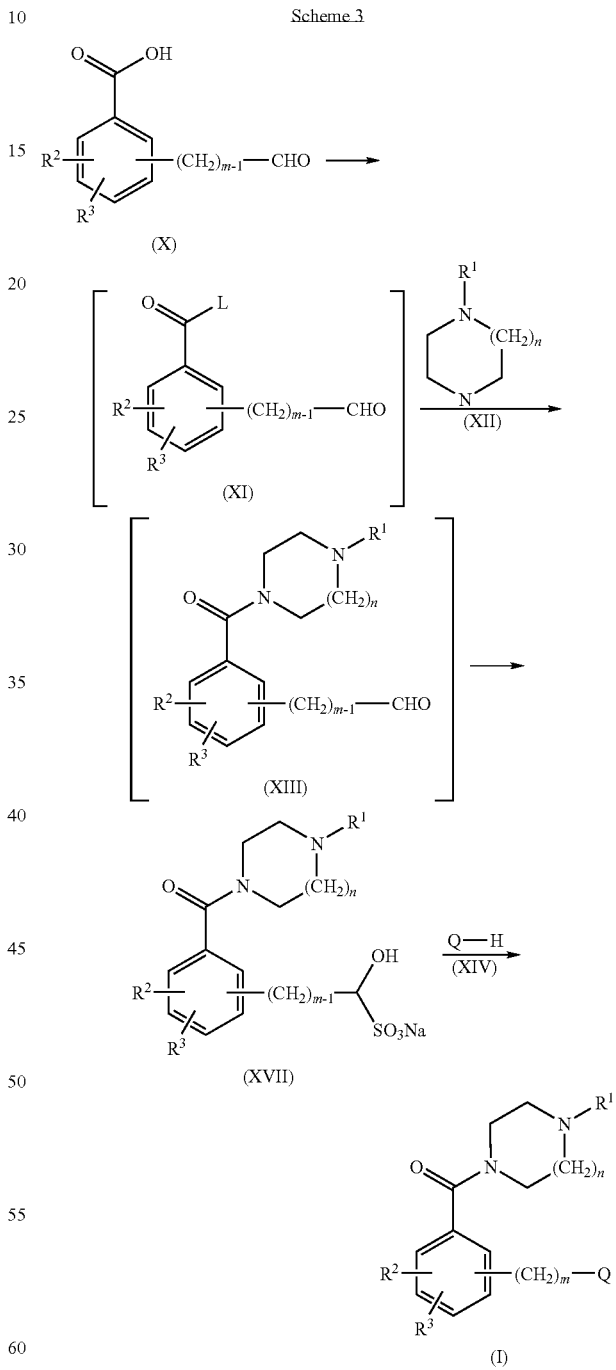

Accordingly, a suitably substituted compound of formula (X), a known compound or compound prepared by known methods, is activated according to known methods, to yield the corresponding compound of formula (XI), wherein L is a suitable leaving group such as chloro, bromo, —OC(O)O—

$C_{1-4}$alkyl, OBt (wherein the activating agent is HOBt), -imidazolide (wherein the activating agent is CDI), and the like; preferably chloro.

For example, wherein L is chloro, the compound of formula (X) is reacted with a suitable chlorinating agent such as oxalyl chloride, thionyl chloride, phosphorus oxychloride, and the like, preferably about 1.05 equivalents of thionyl chloride in the presence of a catalytic amount of DMF; in an organic solvent such as THF, toluene, dichloromethane, dichloroethane, acetonitrile, and the like, preferably THF. Alternatively, the compound of formula (X) is reacted with Vilsmeier's reagent (chloromethylene-dimethyl-ammonium chloride) in an organic solvent such as DCM; at a temperature in the range of from about 0° C. to about room temperature.

Preferably, the compound of formula (XI) is not isolated.

The compound of formula (XI) is reacted with a suitably substituted compound of formula (XII), a known compound or compound prepared by known methods, wherein the compound of formula (XII) is preferably present in an amount equal to about one equivalent, more preferably about 0.95 equivalents; in the presence of an organic or inorganic base (solid or aqueous) such as TEA, DIPEA, pyridine, NaOH, KOH, sodium carbonate, potassium carbonate, and the like, preferably TEA; wherein the base is organic, preferably in the absence of water; in an organic solvent such as THF, toluene, acetonitrile, and the like, preferably THF; to yield the corresponding compound of formula (XIII).

Preferably, the compound of formula (XIII) is not isolated.

The compound of formula (XIII) is reacted with a suitable source of bisulfite such as $NaHSO_3$, $KHSO_3$, and the like, preferably aqueous $NaHSO_3$; wherein the source of bisulfite is preferably present in an amount greater than or equal to about one equivalent, more preferably in an amount in range of from about 1 to about 2 equivalents, more preferably still in an amount equal to about 1.2 equivalents; in a polar organic solvent such as methanol, ethanol, THF, DMF, acetonitrile, and the like, preferably ethanol; to yield the corresponding bisulfite, the compound of formula (XVII).

Preferably, the compound of formula (XVII) is isolated by known methods, for example by filtration and washing with a suitable organic solvent such ethanol, hexane, and the like; and then further, optionally purified, by known methods, for example by recrystallization from a suitable solvent such as methanol, ethanol, isopropanol, acetonitrile, and the like, preferably ethanol.

The compound of formula (XVII) is reacted in a 2-step or 1-step process, wherein the bisulfite is reacted to liberate the corresponding aldehyde, the compound of formula (XIII) and the aldehyde compound of formula (XIII) is reacted with the compound of formula (XIV) to yield the corresponding compound of formula (I).

More specifically, the compound of formula (XVII) is reacted with a suitably substituted compound of formula (XIV), a known compound or compound prepared by known methods, wherein the compound of formula (XIV) is preferably present in an amount greater than about one equivalent, more preferably in an amount in the range of from about 1 to about 2 equivalents; more preferably still, about 2 equivalents; in the presence of a reducing agent such as $NaBH(OAc)_3$, $NaBH_4$, sodium cyanoborohydride, and the like, preferably, $NaBH(OAc)_3$; wherein the reducing agent is preferably present in an amount in the range of from about 1 to about 2 equivalents, more preferably in an amount in the range of from about 1.25 to about 1.5 equivalents; in the presence of an organic or inorganic base such as TEA, DIPEA, pyridine, NaOH, KOH, and the like, preferably 10% aqueous NaOH; in an organic solvent such as dichloroethane, THF, toluene, acetonitrile, and the like, preferably, dichloroethane; optionally in the presence of a source of acid such as the acid clay Montmorillonite K-10 (available from Aldrich), Nafion-H (CA Reg. No. 63937-00-8), and the like; to yield the corresponding compound of formula (I).

One skilled in the art will recognize that wherein the amount of the compound of formula (XIV) is greater than or equal to about 2 equivalents, then one equivalent of the compound of formula (XIV) acts as the organic or inorganic base to liberate the aldehyde, the compound of formula (XIII) and therefore, additional organic or inorganic base is not necessary.

Alternatively, the compound of formula (XVII) is reacted with an organic or inorganic base such as TEA, DIPEA, pyridine, NaOH, KOH, and the like, preferably 10% aqueous NaOH; wherein the base is preferably present in an amount greater than or equal to about 1 equivalent, more preferably in an amount in the range of from about 1 to about 2 equivalents; according to known methods to remove the bisulfite and liberate the corresponding compound of formula (XIII).

The compound of formula (XIII) is then reacted with a suitably substituted compound of formula (XIV), wherein the compound of formula (XIV) is preferably present in an amount greater than or equal to about 1 equivalent, preferably in an amount in the range of form about 1 to about 2 equivalents; in the presence of a reducing agent such as $NaBH(OAc)_3$, $NaBH_4$, sodium cyanoborohydride, and the like, preferably, $NaBH(OAc)_3$; wherein the reducing agent is preferably present in an amount in the range of from about 1 to about 2 equivalents, more preferably in an amount in the range of from about 1.25 to about 1.5 equivalents; optionally in the presence of a source of acid such as the acid clay Montmorillonite K-10 (available from Aldrich), Nafion-H (CA Reg. No. 63937-00-8), and the like; in an organic solvent such as THF, toluene, acetonitrile, and the like, preferably, THF; to yield the corresponding compound of formula (I).

Alternatively, the compound of formula (XIII) is reacted with a suitably substituted compound of formula (XIV) according to the methods as described herein or as described in US Patent Application Publication 2004-0010746 A1, to yield the corresponding compound of formula (I).

Preferably, the compound of formula (I) is isolated according to known methods, for example by solvent evaporation. The compound of formula (I) may be further, optionally, reacted according to known methods, to yield its corresponding pharmaceutically acceptable salt.

In an embodiment, the present invention is directed to improvements in the process disclosed in US Patent Application Publication 2004-0010746 A1 for the preparation of the compound of formula (Is), also known as (4-isopropyl-piperazin-1-yl)-(4-morpholin-4-ylmethyl-phenyl)-methanone, as described in more detail in Scheme 4 below.

Scheme 4

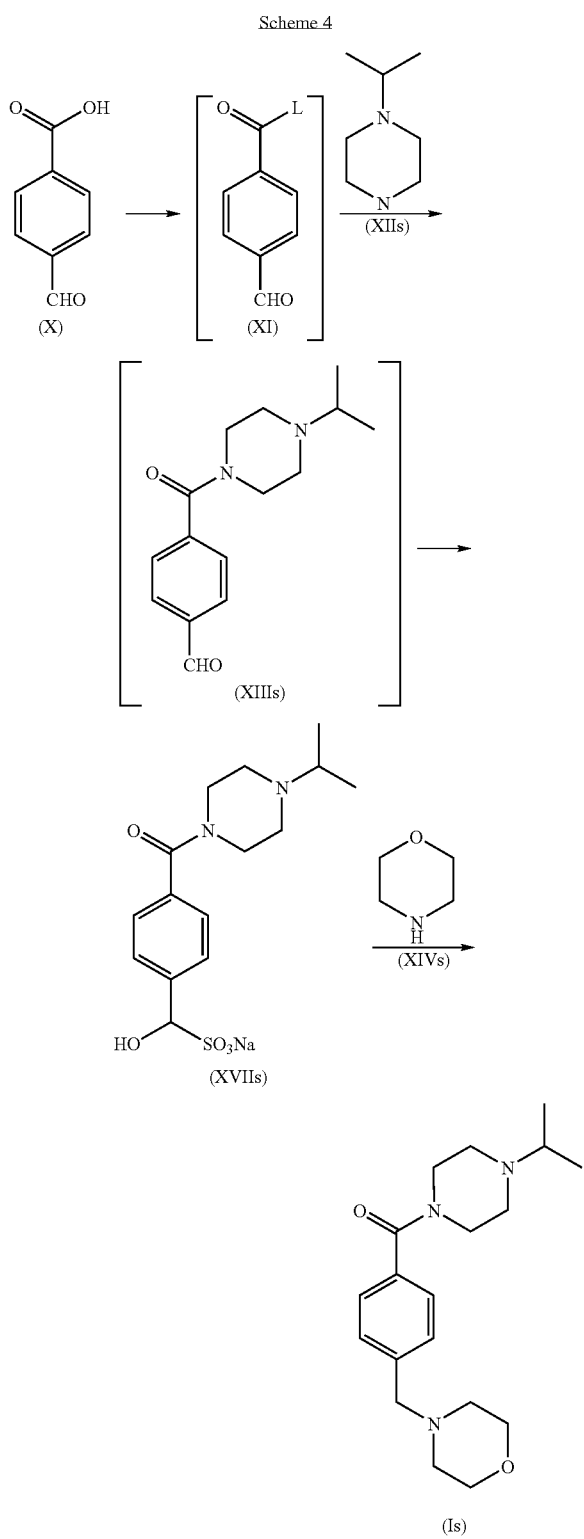

Accordingly, a suitably substituted compound of formula (Xs), also known as 4-formyl-benzaldehyde, a known compound, is activated according to known methods, to yield the corresponding compound of formula (XIs), wherein L is a suitable leaving group such as chloro, bromo, —OC(O)O— $C_{1-4}$alkyl, OBt (wherein the activating agent is HOBt), -imidazolide (wherein the activating agent is CDI), and the like; preferably chloro.

For example, wherein L is chloro, the compound of formula (Xs) is reacted with a suitable chlorinating agent such as oxalyl chloride, thionyl chloride, phosphorus oxychloride, and the like, preferably about 1.05 equivalents of thionyl chloride in the presence of a catalytic amount of DMF in an organic solvent such as THF, toluene, dichloromethane, dichloroethane, acetonitrile, and the like, preferably THF. Alternatively, the compound of formula (Xs) is reacted with Vilsmeier's reagent (chloromethylene-dimethyl-ammonium chloride) in an organic solvent such as DCM; at a temperature in the range of from about 0° C. to about room temperature.

Preferably, the compound of formula (XIs) is not isolated.

The compound of formula (XIs) is reacted with a suitably substituted compound of formula (XIIs), also known as 4-isopropylpiperazine, a known compound, wherein the compound of formula (XIIs) is preferably present in an amount equal to about one equivalent, more preferably about 0.95 equivalents; in the presence of an organic or inorganic base (solid or aqueous) such as TEA, DIPEA, pyridine, NaOH, KOH, sodium carbonate, potassium carbonate, and the like, preferably TEA; wherein the base is organic, preferably in the absence of water; in an organic solvent such as THF, toluene, acetonitrile, and the like, preferably THF; to yield the corresponding compound of formula (XIIIs).

Preferably, the compound of formula (XIIIs) is not isolated.

The compound of formula (XIIIs) is reacted with a suitable source of bisulfite such as $NaHSO_3$, $KHSO_3$, and the like, preferably aqueous $NaHSO_3$; wherein the source of bisulfite is preferably present in an amount greater than or equal to about one equivalent, more preferably in an amount in range of from about 1 to about 2 equivalents, more preferably still in an amount equal to about 1.2 equivalents; in a polar organic solvent such as methanol, ethanol, THF, DMF, acetonitrile, and the like, preferably ethanol; to yield the corresponding bisulfite, the compound of formula (XVIIs).

Preferably, the compound of formula (XVIIs) is isolated by known methods, for example by filtration and washing with a suitable organic solvent such ethanol, hexane, and the like; and then further, optionally purified, by known methods, for example by recrystallization from a suitable solvent such as methanol, ethanol, isopropanol, acetonitrile, and the like, preferably ethanol.

The compound of formula (XVIIs) is reacted in a 2-step or 1-step process, wherein the bisulfite is reacted to liberate the corresponding aldehyde, the compound of formula (XIIIs) and the aldehyde compound of formula (XIIIs) is reacted with the compound of formula (XIVS) to yield the corresponding compound of formula (Is).

More specifically, the compound of formula (XVIIs) is reacted with a suitably substituted compound of formula (XIVs), also known as morpholine, a known compound, wherein the compound of formula (XIVs) is preferably present in an amount greater than about one equivalent, more preferably in an amount in the range of from about 1 to about 2 equivalents; more preferably still, about 2 equivalents; in the presence of a reducing agent such as $NaBH(OAc)_3$, $NaBH_4$, sodium cyanoborohydride, and the like, preferably, $NaBH(OAc)_3$; wherein the reducing agent is preferably present in an amount in the range of from about 1 to about 2 equivalents, more preferably in an amount in the range of from about 1.25 to about 1.5 equivalents; in the presence of an organic or inorganic base such as TEA, DIPEA, pyridine, NaOH, KOH, and the like, preferably 10% aqueous NaOH; in an organic solvent such as dichloroethane, THF, toluene, acetonitrile, and the like, preferably, dichloroethane; optionally in the presence of a source of acid such as the acid clay Montmorillonite K-10 (available from Aldrich), Nafion-H (CA Reg. No. 63937-00-8), and the like; to yield the corresponding compound of formula (Is).

One skilled in the art will recognize that wherein the amount of the compound of formula (XIVs) is greater than or equal to about 2 equivalents, then one equivalent of the compound of formula (XIVs) acts as the organic or inorganic base to liberate the aldehyde, the compound of formula (XIIIs) and therefore, additional organic or inorganic base is not necessary.

Alternatively, the compound of formula (XVIIs) is reacted with an organic or inorganic base such as TEA, DIPEA, pyridine, NaOH, KOH, and the like, preferably 10% aqueous NaOH; wherein the base is preferably present in an amount greater than or equal to about 1 equivalent, more preferably in an amount in the range of from about 1 to about 2 equivalents; according to known methods to remove the bisulfite and liberate the corresponding compound of formula (XIIIs).

The compound of formula (XIIs) is then reacted with a suitably substituted compound of formula (XIVs), wherein the compound of formula (XIVs) is preferably present in an amount greater than or equal to about 1 equivalent, preferably in an amount in the range of form about 1 equivalent to about 2 equivalents; in the presence of a reducing agent such as NaBH(OAc)$_3$, NaBH$_4$, sodium cyanoborohydride, and the like, preferably, NaBH(OAc)$_3$; wherein the reducing agent is preferably present in an amount in the range of from about 1 to about 2 equivalents, more preferably in an amount in the range of from about 1.25 to about 1.5 equivalents; optionally in the presence of a source of acid such as the acid clay Montmorillonite K-10 (available from Aldrich), Nafion-H (CA Reg. No. 63937-00-8), and the like; in an organic solvent such as THF, toluene, acetonitrile, and the like, preferably, THF; to yield the corresponding compound of formula (Is).

Alternatively, the compound of formula (XIIIs) is reacted with a suitably substituted compound of formula (XIVs) according to the methods as described herein or as described in US Patent Application Publication 2004-0010746 A1, to yield the corresponding compound of formula (Is).

Preferably, the compound of formula (Is) is isolated according to known methods, for example by solvent evaporation. The compound of formula (Is) may be further, optionally, reacted according to known methods, to yield its corresponding pharmaceutically acceptable salt, preferably, its corresponding mono-succinate salt.

The present invention is further directed to novel crystalline salts of the compound of formula (I). In an embodiment, the present invention is directed to a maleate, fumarate, succinate, hydrochloride or hydrobromide salt of the compound of formula (I).

The present invention is further directed to novel crystalline salts of the compound of formula (Is). In an embodiment, the present invention is directed to a maleate, fumarate, succinate, hydrochloride or hydrobromide salt of the compound of formula (Is).

In an embodiment, the present invention is directed to a crystalline succinate salt of the compound of formula (Is). In another embodiment, the crystalline succinate salt of the compound of formula (Is) is a mono-succinate salt. The crystalline mono-succinate salt of the compound of formula (Is) is non-hygroscopic. The mono-succinate salt of the compound of formula (Is) was determined to be crystalline by XRD and DSC; and non-hygroscopic by DVS.

The crystalline mono-succinate salt of the compound of formula (Is) may be represented by the following chemical structure:

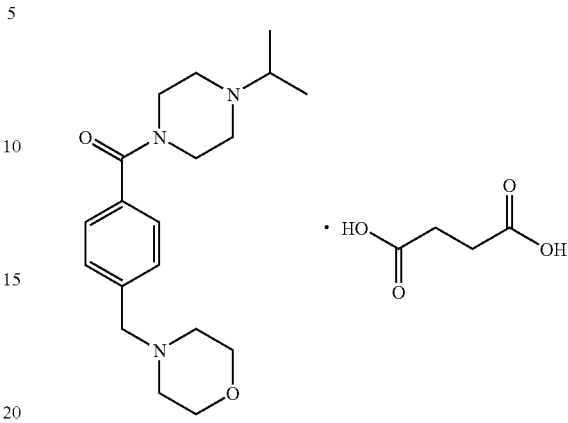

The crystalline succinate salt of the compound of formula (Is) may be prepared by reacting the compound of formula (Is) with succinic acid; wherein the succinic acid is preferably present in an amount in the range of from about 1 to about 2 equivalents, more preferably about 1.3 equivalents; in an organic solvent such as THF, toluene, acetonitrile, and the like, preferably in an organic solvent in which succinic acid is soluble, more preferably in THF.

The crystalline succinate salt of the compound of formula (Is) is preferably purified according to known methods, more preferably by recrystallization from a suitable solvent such as absolute ethanol, methanol, isopropyl alcohol, acetonitrile, and the like, preferably from absolute ethanol.

The present invention is further directed to a pharmaceutically acceptable salt of the compound of formula (Is) wherein the salt is a maleate, fumarate, hydrochloride or hydrobromide salt of the compound of formula (Is). In another embodiment, the salt of the compound of formula (Is) is a bis-maleate, mono-fumarate, di-hydrochloride or di-hydrobromide salts of the compound of formula (Is). The bis-maleate, mono-fumarate, di-hydrochloride and di-hydrobromide salts of the compound of formula (Is) may be prepared by reacting the compound of formula (Is) with the corresponding acid (i.e. maleic acid, fumaric acid, HCl and HBr, respectively), as described in more detail in the Examples which follow herein.

The bis-maleate salt of the compound of formula (Is) was determined to be crystalline by XRD and DSC; and hygroscopic by DVS. The fumarate salt of the compound of formula (Is) was determined to be crystalline by XRD and DSC; and stable at relative humidities of up to about 70% by DVS. The di-hydrochloride salt of the compound of formula (Is) was determined to be partially crystalline by XRD and DSC; and a mono-hydrate by Karl-Fisher and hygroscopic by DVS. The di-hydrobromide salt of the compound of formula (Is) was determined to be partially crystalline by XRD and DSC; a semi-hydrate by Karl-Fisher; and hygroscopic above about 10% RH by DVS.

The salts of the compound of formula (Is) may be characterized by their corresponding powder X-ray diffraction pattern. The X-ray diffraction patterns listed herein were measured using an X-Celerator detector. The sample was backloaded into a conventional x-ray holder and scanned from 3 to 35°2θ with a step size of 0.0165°2θ and a time per step of 10.16 seconds. The effective scan speed was 0.2067°/s. Instrument voltage and current settings were 45 kV and 40 mA.

The crystalline mono-succinate salt of the compound of formula (Is) may be characterized by its X-ray diffraction pattern, comprising the peaks as listed in Table 1, below.

TABLE 1

| Position [°2θ] | d-spacing [Å] | Relative Intensity [%] |
| --- | --- | --- |
| 8.782 | 10.0698 | 100.00 |
| 13.161 | 6.7274 | 62.86 |
| 14.587 | 6.0728 | 13.50 |
| 15.961 | 5.5527 | 21.15 |
| 17.308 | 5.1237 | 24.32 |
| 17.555 | 5.0520 | 46.94 |
| 19.767 | 4.4915 | 22.73 |
| 20.210 | 4.3941 | 19.15 |
| 20.415 | 4.3503 | 19.40 |
| 23.802 | 3.7383 | 48.59 |
| 26.429 | 3.3728 | 49.97 |

Preferably, the crystalline mono-succinate salt of the compound of formula (Is) is characterized by its XRD pattern which comprises peaks having a relative intensity greater than or equal to about 25%, as listed in Table 2 below.

TABLE 2

| Position [°2θ] | d-spacing [Å] | Relative Intensity [%] |
| --- | --- | --- |
| 8.782 | 10.0698 | 100.00 |
| 13.161 | 6.7274 | 62.86 |
| 17.555 | 5.0520 | 46.94 |
| 23.802 | 3.7383 | 48.59 |
| 26.429 | 3.3728 | 49.97 |

In an embodiment, the crystalline, mono-succinate salt of the compound of formula (Is) is characterized by the peak positions (in °2θ) in its XRD spectra for peaks with a relative intensity greater than about 10%, preferably with a relative intensity greater than about 25%.

The crystalline mono-fumarate salt of the compound of formula (Is) may be characterized by its X-ray diffraction pattern, comprising the peaks as listed in Table 3, below.

TABLE 3

| Position [°2θ] | d-spacing [Å] | Relative Intensity [%] |
| --- | --- | --- |
| 9.164 | 9.6501 | 68.78 |
| 13.652 | 6.4862 | 98.14 |
| 18.182 | 4.8791 | 74.48 |
| 20.318 | 4.3708 | 24.49 |
| 22.682 | 3.9204 | 11.12 |
| 24.146 | 3.6859 | 35.43 |
| 24.529 | 3.6293 | 60.71 |
| 25.361 | 3.5121 | 12.35 |
| 27.081 | 3.2928 | 85.98 |
| 27.330 | 3.2633 | 100.00 |
| 28.644 | 3.1165 | 19.53 |
| 28.813 | 3.0986 | 12.99 |
| 31.889 | 2.806 | 19.76 |
| 31.971 | 2.799 | 12.26 |

Preferably, the crystalline mono-fumarate salt of the compound of formula (Is) is characterized by its XRD pattern which comprises peaks having a relative intensity greater than or equal to about 25%, as listed in Table 4 below.

TABLE 4

| Position [°2θ] | d-spacing [Å] | Relative Intensity [%] |
| --- | --- | --- |
| 9.164 | 9.6501 | 68.78 |
| 13.652 | 6.4862 | 98.14 |
| 18.182 | 4.8791 | 74.48 |
| 24.146 | 3.6859 | 35.43 |
| 24.529 | 3.6293 | 60.71 |
| 27.081 | 3.2928 | 85.98 |
| 27.330 | 3.2633 | 100.00 |

In an embodiment, the crystalline, mono-fumarate salt of the compound of formula (Is) is characterized by the peak positions (in °2θ) in its XRD spectra for peaks with a relative intensity greater than about 10%, preferably with a relative intensity greater than about 25%.

The crystalline di-hydrochloride salt of the compound of formula (Is) may be characterized by its X-ray diffraction pattern, comprising the peaks as listed in Table 5, below.

TABLE 5

| Position [°2θ] | d-spacing [Å] | Relative Intensity [%] |
| --- | --- | --- |
| 5.648 | 15.6651 | 12.12 |
| 11.220 | 7.8862 | 27.02 |
| 15.418 | 5.7471 | 23.03 |
| 15.789 | 5.6130 | 47.14 |
| 16.268 | 5.4485 | 53.50 |
| 16.726 | 5.3005 | 38.75 |
| 17.268 | 5.1353 | 16.41 |
| 17.565 | 5.0491 | 21.51 |
| 17.955 | 4.9410 | 14.80 |
| 18.900 | 4.6955 | 19.52 |
| 19.494 | 4.5536 | 45.87 |
| 21.809 | 4.0753 | 100.00 |
| 22.452 | 3.9601 | 35.06 |
| 22.894 | 3.8845 | 22.57 |
| 23.394 | 3.8027 | 29.19 |
| 24.955 | 3.5683 | 35.07 |
| 25.544 | 3.4873 | 27.86 |
| 26.116 | 3.4122 | 34.92 |
| 27.902 | 3.1977 | 35.17 |
| 28.710 | 3.1096 | 16.28 |
| 31.481 | 2.8418 | 31.54 |

Preferably, the crystalline di-hydrochloride salt of the compound of formula (Is) is characterized by its XRD pattern which comprises peaks having a relative intensity greater than or equal to about 25%, as listed in Table 6 below.

TABLE 6

| Position [°2θ] | d-spacing [Å] | Relative Intensity [%] |
| --- | --- | --- |
| 11.220 | 7.8862 | 27.02 |
| 15.789 | 5.6130 | 47.14 |
| 16.268 | 5.4485 | 53.50 |
| 16.726 | 5.3005 | 38.75 |
| 19.494 | 4.5536 | 45.87 |
| 21.809 | 4.0753 | 100.00 |
| 22.452 | 3.9601 | 35.06 |
| 23.394 | 3.8027 | 29.19 |
| 24.955 | 3.5683 | 35.07 |
| 25.544 | 3.4873 | 27.86 |
| 26.116 | 3.4122 | 34.92 |
| 27.902 | 3.1977 | 35.17 |
| 31.481 | 2.8418 | 31.54 |

In an embodiment, the crystalline, di-hydrochloride salt of the compound of formula (Is) is characterized by the peak positions (in °2θ) in its XRD spectra for peaks with a relative intensity greater than about 10%, preferably with a relative intensity greater than about 25%.

The crystalline di-hydrobromide salt of the compound of formula (Is) may be characterized by its X-ray diffraction pattern, comprising the peaks as listed in Table 7, below.

TABLE 7

| Position [°2θ] | d-spacing [Å] | Relative Intensity [%] |
|---|---|---|
| 11.386 | 7.7720 | 50.80 |
| 16.194 | 5.4735 | 10.38 |
| 16.744 | 5.2949 | 21.92 |
| 17.071 | 5.1943 | 39.18 |
| 18.391 | 4.8244 | 100.00 |
| 19.019 | 4.6665 | 39.71 |
| 20.105 | 4.4167 | 13.60 |
| 21.462 | 4.1404 | 37.22 |
| 22.641 | 3.9274 | 22.33 |
| 22.961 | 3.8735 | 58.57 |
| 24.407 | 3.6471 | 29.56 |
| 24.676 | 3.6079 | 41.54 |
| 25.189 | 3.5356 | 96.54 |
| 27.094 | 3.2912 | 15.39 |
| 28.080 | 3.1778 | 11.46 |
| 32.02 | 2.9808 | 12.84 |
| 30.665 | 2.9156 | 32.02 |
| 31.292 | 2.8586 | 29.78 |
| 31.765 | 2.8171 | 17.27 |

Preferably, the crystalline di-hydrobromide salt of the compound of formula (Is) is characterized by its XRD pattern which comprises peaks having a relative intensity greater than or equal to about 25%, as listed in Table 8 below.

TABLE 8

| Position [°2θ] | d-spacing [Å] | Relative Intensity [%] |
|---|---|---|
| 11.386 | 7.7720 | 50.80 |
| 17.071 | 5.1943 | 39.18 |
| 18.391 | 4.8244 | 100.00 |
| 19.019 | 4.6665 | 39.71 |
| 21.462 | 4.1404 | 37.22 |
| 22.961 | 3.8735 | 58.57 |
| 24.407 | 3.6471 | 29.56 |
| 24.676 | 3.6079 | 41.54 |
| 25.189 | 3.5356 | 96.54 |
| 30.665 | 2.9156 | 32.02 |
| 31.292 | 2.8586 | 29.78 |

In an embodiment, the crystalline, di-hydrobromide salt of the compound of formula (Is) is characterized by the peak positions (in °2θ) in its XRD spectra for peaks with a relative intensity greater than about 10%, preferably with a relative intensity greater than about 25%.

The compounds or compositions of the invention may be formulated and administered to a subject by any conventional route of administration, including, but not limited to, intravenous, oral, subcutaneous, intramuscular, intradermal and parenteral administration. The quantity of the compound which is effective for treating each condition may vary, and can be determined by one of ordinary skill in the art.

The present invention also provides pharmaceutical compositions comprising one or more compounds of this invention in association with a pharmaceutically acceptable carrier and optionally additional pharmaceutical agents such as $H_1$ antagonists or SSRIs (Selective Serotonin Reuptake Inhibitors). Preferably these compositions are in unit dosage forms such as pills, tablets, caplets, capsules (each including immediate release, timed release and sustained release formulations), powders, granules, sterile parenteral solutions or suspensions (including syrups and emulsions), metered aerosol or liquid sprays, drops, ampoules, autoinjector devices or suppositories; for oral, parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid pre-formulation composition containing a homogeneous mixture of a compound of the present invention, or a pharmaceutically acceptable salt thereof. When referring to these pre-formulation compositions as homogeneous, it is meant that the active ingredient is dispersed evenly throughout the composition so that the composition may be readily subdivided into equally effective dosage forms such as tablets, pills and capsules. This solid pre-formulation composition is then subdivided into unit dosage forms of the type described above containing from 5 to about 1000 mg of the active ingredient of the present invention. Examples include 5 mg, 7 mg, 10 mg, 15 mg, 20 mg, 35 mg, 50 mg, 75 mg, 100 mg, 120 mg, 150 mg, and so on. The tablets or pills of the disclosed compositions can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the compounds and compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment is required.

The daily dosage of the products may be varied over a wide range from 1 to 1,000 mg per adult human per day. For oral administration, the compositions are preferably provided in the form of tablets containing 1.0, 5.0, 10.0, 15.0, 25.0, 50.0, 100, 250 and 500 milligrams of the active ingredient for the symptomatic adjustment of the dosage to the subject to be treated. An effective amount of the drug is ordinarily supplied at a dosage level of from about 0.01 mg/kg to about 20 mg/kg of body weight per day. Preferably, the range is from about 0.02 mg/kg to about 10 mg/kg of body weight per day, and especially from about 0.05 mg/kg to about 10 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

EXAMPLE 1

4-Formyl-benzoyl chloride

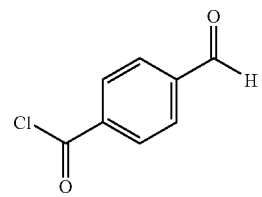

To a thin suspension of 4-carboxybenzaldehyde (600 g, 3.92 mol) in tetrahydrofuran (2664 g, 36.57 mol) was added dimethylformadehyde (11.48 g, 0.16 mol) and the reaction mixture was cooled to 0-5° C. with an ice bath. The reaction mixture was then stirred at 0° C. while oxalyl chloride (608.69 g, 4.70 mol) was added slowly. The reaction mixture was stirred until it was deemed complete by $^1$HNMR to yield the title compound. The reaction mixture was used in the next step without further manipulation.

$^1$HNMR (CDCl3): 10.15 (s, 1H), 8.35 (d, 2H), 8.05 (d, 2H)

EXAMPLE 2

4-(4-Isopropyl-piperazine-1-carbonyl)-benzaldehyde

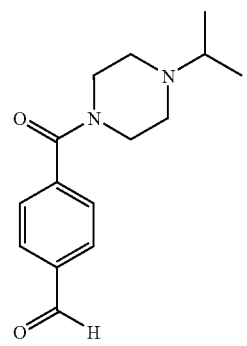

A solution of 4-formyl-benzoyl chloride (2.80, 16.65 mol) (prepared as in Example 1 above) in toluene (43.3 g, 469.39 mmol) was added slowly to a solution of NaHCO$_3$ (0.8 g, 9.52 mmol) and 4-isopropylpiperazine (2.50 g, 18.35 mmol) in water (5 g, 277 mmol) at 0° C. The reaction mixture was vigorously stirred until the reaction was deemed complete. The layers were split and the toluene phase was concentrated to yield the title compound as a yellow oil.

$^1$HNMR (CDCl3): 10.15 (s, 1 H), 7.95 (d, 2H), 7.55 (d, 2H), 3.75 (br s, 2H), 3.40 (br s, 2H), 2.75 (m, 1H), 2.55 (br s, 2H), 2.41 (br s, 2H), 1.09 (d, 6H)

EXAMPLE 3

4-(4-Isopropyl-piperazine-1-carbonyl)-benzaldehyde

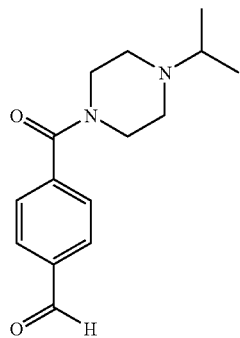

4-Isopropyl-piperazine (79.53 g, 0.620 mol), THF (444 g, 5.04 mol), water (36 g, 2 mol) and a 50% solution of sodium hydroxide (130.6 g, 1.63 mol) were charged to a reaction vessel and cooled to 0-5° C. 4-Formyl-benzoyl chloride in THF (110.08 g, 0.630 mol) was added to the 4-isopropyl-piperazine reaction mixture while maintaining the temperature below about 10° C. The resulting white suspension was stirred at room temperature until the reaction was deemed complete. Water was added to the reaction slurry and the resulting hazy solution was filtered over Celite to remove insolubles. The filtered reaction solution was settled and the water layer was removed. The product/THF layer was dried sequentially with magnesium sulfate and molecular sieves. The product solution (KF≦0.5%) was stored at 5° C. for use without further manipulations.

EXAMPLE 4

(4-Isopropyl-piperazin-1-yl)-(4-morpholin-4-ylmethyl-phenyl)-methanone

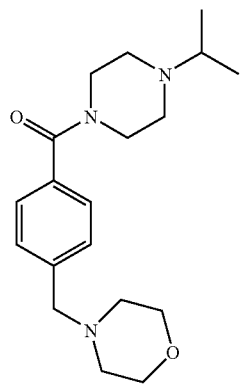

To a solution of 4-(4-isopropyl-piperazine-1-carbonyl)-benzaldehyde (4.0 g, 15.38 mmol) in THF (40 mL) was added morpholine (2.9 g, 33.83 mmol), and the resulting mixture was stirred at room temperature for 1 h before it was cooled to 0° C. with an ice bath. The reaction mixture was then treated with NaBH(OAc)$_3$ (4.56 g, 21.53 mmol) in portions over 15 min. The resulting suspension was stirred at room temperature until it was deemed complete by HPLC. After completion, 10% NaOH (25 mL) was added and the reaction was vigorously agitated for 15 min. The phases were separated and the aqueous layer was extracted with THF (20 mL). The organic layers were combined, dried (MgSO$_4$), filtered and concentrated to yield the title compound as a yellow oil.

$^1$H NMR (CDCl$_3$): 7.36 (s, 4H), 3.79 (br s, 2H), 3.71 (t, 4H), 3.51 (s, 2H), 3.44 (br s, 2H), 2.76-2.69 (m, 1H), 2.59 (br s, 2H), 2.44 (t, 6H), 1.05 (d, 6H).

EXAMPLE 5

(4-Isopropyl-piperazin-1-yl)-(4-morpholin-4-ylmethyl-phenyl)-methanone

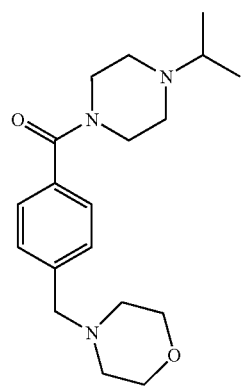

A THF solution of 1-(4-formylbenzoyl)-4-isopropylpiperazine (containing 945 g of 1-(4-formylbenzoyl)-4-isopropylpiperazine and 3879 g of THF) was charged to a reaction vessel followed by the addition of morpholine (576.3 g, 6.55 mol). After 20 min, the reaction was cooled to about 0-10° C. and sodium triacetoxyborohydride (1167.3 g, 5.23 mol) was added in portions. Upon reaction completion, 10% sodium hydroxide solution (3623.2 mL, 9.06 mol) was added slowly and the reaction mixture was stirred for 20 min. The layers were separated, and the aqueous layer was washed with THF. The combined organic layers were dried over magnesium sulfate. The dried THF solution of (4-Isopropyl-piperazin-1-yl)-(4-morpholin-4-ylmethyl-phenyl)-methanone was used without further manipulations.

EXAMPLE 6

(4-Isopropyl-piperazin-1-yl)-(4-morpholin-4-ylmethyl-phenyl)-methanone Mono-succinate Salt

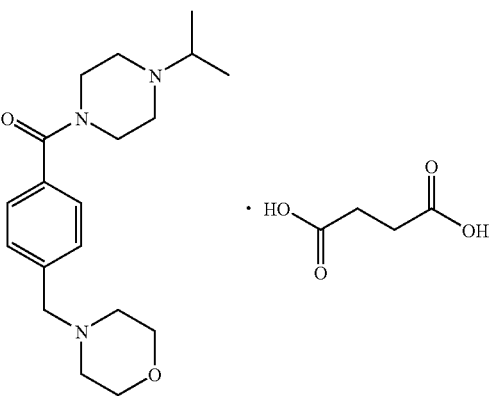

A THF solution (278.0 g) of crude (4-isopropyl-piperazin-1-yl)-(4-morpholin-4-ylmethyl-phenyl)-methanone (59.4 g, 0.179 mol) was heated to 40° C. and succinic acid (27.53 g, 0.233 mol) was added. The reaction mixture was heated to 60° C. and filtered into a clean flask. The resulting solution was re-heated to 60° C. and then cooled slowly, first to room temperature and then to −7° C. The resulting suspension was held at −7° C. and filtered. The filter cake was washed with THF (60 mL) and the solid was dried overnight at 50° C. under full vacuum to yield crude mono-succinate salt as a white solid.

A suspension of the crude mono-succinate salt (701.3 g, 1.56 mol) in ethanol (7.01 L) was heated to 60-65° C. Any insoluble material was removed by filtration. The resulting clear solution was cooled slowly to −7° C. The slurry was filtered and washed with ethanol (700 mL). The filter cake was dried overnight at 50° C. under full vacuum to yield the mono-succinate salt as a white crystalline solid.

M.P.: 154-156° C.
Elemental Analysis For $C_{19}H_{29}N_3O_2 \times C_4H_6O_2$:
Calculated: C, 61.45; H, 7.85; N, 9.35; $H_2O$, <0.1%.
Found: C, 61.42; H, 7.84; N, 9.29; $H_2O$, <0.1%.
MS: $[M+H]^+=332$; $[2M+H]^+=685$.

EXAMPLE 7

(4-Isopropyl-piperazin-1-yl)-(4-morpholin-4-ylmethyl-phenyl)-methanone Mono-fumarate Salt

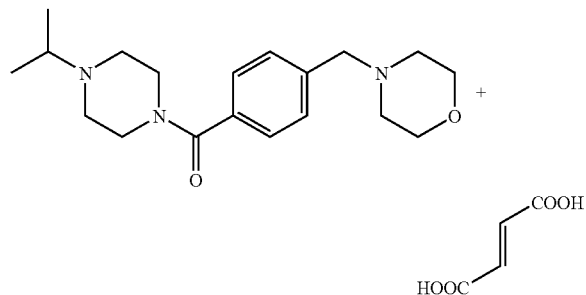

To a THF solution (40 mL) of (4-isopropyl-piperazin-1-yl)-(4-morpholin-4-ylmethyl-phenyl)-methanone (3.0 g, 9.0 mmol) were added THF (40 mL) and fumaric acid (3.3 g, 28.4 mmol). The resulting mixture was heated to 60° C. and stirred for 0.5 h. The resulting suspension was cooled to 0° C. and the resulting precipitate was collected by filtration, washed with THF (20 mL), and dried in a vacuum oven at 65° C. for 20 h to yield crude title compound as a white solid.

A suspension of crude (4-isopropyl-piperazin-1-yl)-(4-morpholin-4-ylmethyl-phenyl)-methanone, mono-fumarate (5.7 g, 12.7 mmol) in absolute EtOH (110 mL) was heated to 70° C. Any insoluble material was removed by filtration through a Celite pad. The filtrate was reheated to 65° C. and then cooled to 0° C. The precipitate was collected by filtration and washed with MTBE (20 mL). The solids were dried in a vacuum oven at 65° C. for 20 h to yield the title compound as a white solid.

M.P.: 196-198° C.
Elemental Analysis for $C_{19}H_{29}N_3O_2 \times C_4H_4O_4$:
Calculated: C, 61.73; H, 7.43; N, 9.39.
Found: C, 61.44; H, 7.50; N, 9.30.

EXAMPLE 8

(4-Isopropyl-piperazin-1-yl)-(4-morpholin-4-ylmethyl-phenyl)-methanone, dihydrochloride monohydrate salt

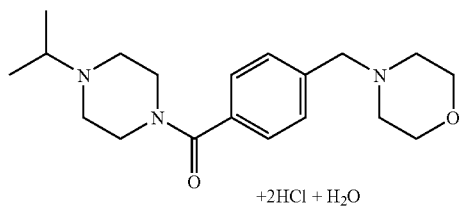

A solution of (4-isopropyl-piperazin-1-yl)-(4-morpholin-4-ylmethyl-phenyl)-methanone (2.0 g, 6.0 mmol) in absolute EtOH (20 mL) was treated with $HCl_{(g)}$ (0.5 g, 13.7 mmol) at room temperature. The resulting suspension was stirred for 1 h, and then MTBE (5 mL) was added. The suspension was cooled to 0° C. and filtered. The filter cake was washed with MTBE (20 mL), and the solid was dried in a vacuum oven at 60° C. for 20 h to yield crude title compound as a white solid.

A suspension of crude (4-isopropyl-piperazin-1-yl)-(4-morpholin-4-ylmethyl-phenyl)-methanone, dihydrochloride (2.1 g, 5.2 mmol) in absolute EtOH (30 mL) was heated to 78° C. and $H_2O$ (2.2 mL) was added. The resulting solution was cooled to room temperature and MTBE (5 mL) was added. The resulting suspension was cooled to 0° C. and filtered. The filter cake was washed with MeOH (15 mL). The solids were dried in a vacuum oven at 105° C. for 20 h to yield the title compound as a white solid.

M.P.: decomp >220° C.
Elemental Analysis for $C_{19}H_{29}N_3O_2 \times 2HCl \times H_2O$:
Calculated: C, 53.97; H, 7.81; N, 9.94; Cl, 16.81.
Found: C, 54.13; H, 7.50; N, 9.90; Cl, 16.68; KF: 4.02%.

EXAMPLE 9

(4-Isopropyl-piperazin-1-yl)-(4-morpholin-4-ylmethyl-phenyl)-methanone, dihydrobromide semihydrate salt

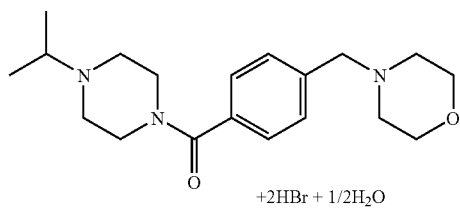

To a THF solution (40 mL) of (4-isopropyl-piperazin-1-yl)-(4-morpholin-4-ylmethyl-phenyl)-methanone (3.0 g, 9.0 mmol) were added THF (40 mL) and 30% hydrogen bromide solution in acetic acid (3.7 mL, 18.6 mmol) while maintaining the temperature between 15° C. and 20° C. The resulting suspension was stirred for 1 h, and then cooled to 0° C. The precipitate was collected by filtration, washed with THF (20 mL), and dried in a vacuum oven at 65° C. for 20 h to yield crude title compound as a white solid.

A suspension of crude (4-isopropyl-piperazin-1-yl)-(4-morpholin-4-ylmethyl-phenyl)-methanone, dihydrobromide (4.9 g, 9.9 mmol) in MeOH (50 mL) was heated to 65° C. The resulting solution was cooled to 0° C. and the precipitate was collected by filtration and washed with MeOH (15 mL). The solids were dried in a vacuum oven at 65° C. for 20 h to yield the title compound as a white solid.

M.P.: >290° C. decomp
Elemental Analysis for $C_{19}H_{29}N_3O_2 \times 2$ HBr×0.5H$_2$O:
Calculated: C, 45.39; H, 6.37; N, 8.36; Br, 31.85.
Found: C, 45.60; H, 6.32; N, 8.36; Br, 33.41.
KF: 2.02%

EXAMPLE 10

(4-Isopropyl-piperazin-1-yl)-(4-morpholin-4-ylmethyl-phenyl)-methanone Bis-maleate Salt

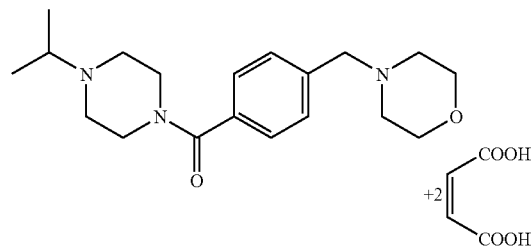

To a solution of (4-isopropyl-piperazin-1-yl)-(4-morpholin-4-ylmethyl -phenyl)-methanone (3.0 g, 9.05 mmol) in absolute EtOH (20 mL) was added, via an addition funnel, a solution of maleic acid (3.3 g, 19.8 mmol) in absolute EtOH (20 mL) over 10 min. The resulting suspension was stirred at room temperature for 15 min, at 75° C. for 30 min, and was then allowed to cool to room temperature for 15 h. The reaction mixture was cooled further to 0° C. and was then stirred for 2 h. The resulting precipitate was collected by suction filtration and washed with cold EtOH (20 mL). The wet solid was dried in a vacuum oven at 40° C. for 6 h to yield the title compound as crude material, as a white solid.

A suspension of the crude (4-isopropyl-piperazin-1-yl)-(4-morpholin-4-ylmethyl-phenyl)-methanone, bis-maleate salt (3.0 g) in absolute EtOH (30 mL) was heated at 75° C. for 1 h, and the resulting solution was filtered through a fine porosity glass frit. The filtrate was heated at 75° C. and then cooled to room temperature over 2 h, with stirring, and Et$_2$O (10 mL) was added. The resulting suspension was cooled to 0° C. for 2 h, the precipitate was collected by suction filtration and washed with Et$_2$O (20 mL) under nitrogen protection. The solids were dried in a vacuum oven at 45° C. for 20 h to yield the title compound as a white crystalline solid.

MP: 154.1° C.
Elemental Analysis for $C_{27}H_{37}N_3O_{10}$:
Calculated: C, 57.54; H, 6.62; N, 7.46.
Found: C, 57.44; H, 6.66; N, 7.33.

EXAMPLE 11

Analysis Protocol for Compounds Prepared as in Examples 12-29

Hewlett Packard HPLC, Zorbax Eclipse XDB-C8, 5 uM, 4.6×150 mm column; Solvents used were H$_2$O/CH$_3$CN/ 0.05% Trifluoroacetic Acid; Gradient conditions were 1%-99% CH$_3$CN gradient over 8 min, 99% CH$_3$CN for 2 min.

All reactions were carried out under a nitrogen atmosphere.

Mass spectra were obtained on an Agilent series 1100 MSD using electrospray ionization (ESI) in either positive or negative modes as indicated.

Thin-layer chromatography was performed using Merck silica gel 60 F$_{254}$ 2.5 cm×7.5 cm 250 μm or 5.0 cm×10.0 cm 250 μm pre-coated silica gel plates. Preparative thin-layer chromatography was performed using EM Science silica gel 60 F$_{254}$ 20 cm×20 cm 0.5 mm pre-coated plates with a 20 cm×4 cm concentrating zone.

NMR spectra were obtained on either a Bruker model DPX400 (400 MHz) or DPX500 (500 MHz) spectrometer. The format of the $^1$H NMR data below is: chemical shift in ppm down field of the tetramethylsilane reference (multiplicity, coupling constant J in Hz, integration).

EXAMPLE 12

1-Isopropyl piperazine dihydrochloride

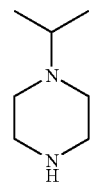

To a solution of tert-butyl piperazine-1-carboxylate (100 g) and acetone (48 mL) in CH$_2$Cl$_2$ (1 L) was added acetic acid (31 mL) and NaBH(OAc)$_3$ (170 g). The reaction mixture was stirred for 18 h, then was diluted with 1 N NaOH (500 mL), and extracted with CH$_2$Cl$_2$ (500 mL×2). The combined organic layers were dried (Na$_2$SO$_4$) and concentrated to a residue. The residue was dissolved in MeOH (200 mL) and 4 M HCl in 1,4-dioxin (700 mL) was added to the reaction mixture over a period of several hours. After 18 h, the reaction mixture was concentrated to yield a solid, which was washed with Et$_2$O (500 mL×2) and dried overnight to yield the title compound as a white solid.

$^1$H NMR (CD$_3$OD): 3.76-3.51 (m, 9H), 1.44 (d, J=6.7 Hz, 6H).

EXAMPLE 13

4-Formyl-benzoyl chloride

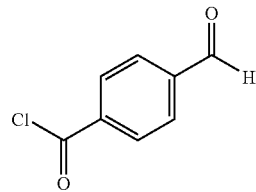

A suspension of (chloromethylene)dimethylammonium chloride (Vilsmeier Reagent; 37.7 g, 0.280 mol) in CH$_2$Cl$_2$ (300 mL) at 0° C. was treated with 4-carboxybenzaldehyde (40.0 g, 267 mmol) in one portion. The reaction mixture was stirred at 0° C. for 30 min, then at room temperature for 2 h.

HPLC analysis of an aliquot of the reaction mixture quenched into MeOH indicated consumption of 4-carboxybenzaldehyde. The reaction mixture was filtered through a medium porosity glass frit. The filtrate, containing the title compound, was stored at 0° C., and used in the next step without further manipulation.

EXAMPLE 14

4-(4-Isopropyl-piperazine-1-carbonyl)-benzaldehyde

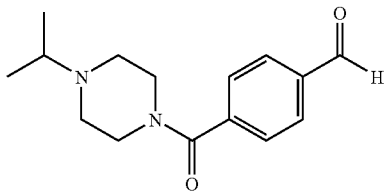

To a suspension of isopropyl piperazine dihydrochloride salt (52.5 g, 262 mmol) (prepared as in Example 12 above) in $CH_2Cl_2$ was added $Et_3N$ (83.5 g, 827 mmol) and the resulting slurry was stirred at room temperature for 1 h, then at 0° C. for 30 min. The reaction mixture was filtered through a medium porosity glass frit and the filtrate was cooled to 0° C. A solution of 4-formyl benzoyl chloride in $CH_2Cl_2$ was added via an addition funnel in a slow stream over 30 min. The resulting mixture was stirred at 0° C. for 30 min, then at room temperature for 2 h. The reaction mixture was cooled to 0° C. and filtered through a medium porosity glass frit. The filtrate was washed with $H_2O$, 0.5 N NaOH, and brine (1×400 mL each). The organic layer was dried ($Na_2SO_4$) and concentrated to yield an oil (59.8 g). Trituration of the oil with anhydrous $Et_2O$ (275 mL), followed by removal of the solvent on a rotary evaporator yielded the title compound as a pale yellow-brown oil.

HPLC: $R_T$=5.43 min.

EXAMPLE 15

Hydroxy-[4-(4-isopropyl-piperazine-1-carbonyl)-phenyl]-methanesulfonic acid sodium salt

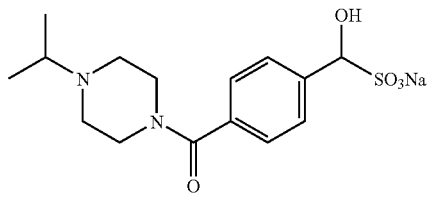

A solution of 4-(4-isopropyl-piperazine-1-carbonyl)-benzaldehyde (20.0 g, 76.9 mmol) in EtOH (200 mL) was stirred at room temperature for 15 min. To the resulting solution was added a solution of $NaHSO_3$ (9.6 g) in $H_2O$ (25 mL), dropwise over 30 min. The resulting suspension was stirred at room temperature for 2 h, then cooled to 0° C. and stirred for 3 h, adding EtOH periodically (total 200 mL) to aid stirring. A precipitate formed and was collected by suction filtration through a glass frit lined with filter paper. The filter cake was washed with hexane (1×50 mL), and dried under vacuum for 16 h to yield the title compound as a white solid.

MP: 275° C. (dec.)

The purity of the compound was determined by dissolution of the bisulfite adduct in 1:1 1 N NaOH/MeOH and analysis by HPLC. In addition, the liberated product was extracted into EtOAc and the organic layer analyzed by TLC (MeOH/$CH_2Cl_2$, 1:9). Prolonged exposure in an iodine chamber indicated a single spot ($R_f$=0.71).

EXAMPLE 16

4-(4-Isopropyl-piperazine-1-carbonyl)-benzaldehyde

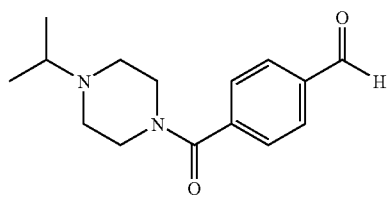

To a suspension of hydroxy-[4-(4-isopropyl-piperazine-1-carbonyl)-phenyl]-methanesulfonic acid sodium salt (49.0 g, 135 mmol) in de-ionized $H_2O$ (490 mL) at 0° C. was added 1 N NaOH (100 mL) in 10 mL portions with vigorous stirring. A clear solution resulted (pH 12), which was stirred at 0° C. for 1 h, then at room temperature for 30 min. The aqueous solution was extracted with EtOAc (3×200 mL), followed by $CH_2Cl_2$ (3×200 mL). The organic layers were combined, washed with brine (1×300 mL), dried ($Na_2SO_4$) and concentrated to yield the title compound as a pale yellow oil.

HPLC: $R_T$=5.43 min

MS (ESI): calcd. for $C_{15}H_{20}N_2O_2$, 260.33; m/z found, 261.1 (M+1)

$^1$H NMR (CDCl$_3$): 10.1 (s, 1H), 7.96 (d, J=8.4 Hz, 2H), 7.45 (d, J=8.3 Hz, 2H), 3.83 (br s, 2H), 3.41 (br s, 2H), 2.78 (m, 1H), 2.64 (br s, 2H), 2.48 (br s, 2H), 1.08 (d, J=6.5 Hz, 6H).

EXAMPLE 17

(4-Isopropyl-piperazin-1-yl)-(4-morpholin-4-ylmethyl-phenyl)-methanone

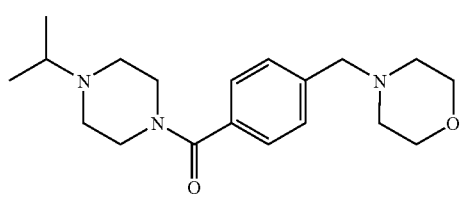

To a solution of 4-(4-isopropyl-piperazine-1-carbonyl)-benzaldehyde (32.0 g, 123 mmol) in THF (650 mL) was added morpholine (21.4 g, 246 mmol), in a slow stream via an addition funnel over 15 min, and the resulting mixture was stirred at room temperature for 40 min. The reaction mixture was treated with NaBH(OAc)$_3$ (38.4 g, 172 mmol) in portions over 40 min, was stirred at room temperature for 16 h, and then concentrated to a residue. The residue was diluted with EtOAc (400 mL), cooled to 0° C., and treated with 1 N NaOH (250 mL). The biphasic solution stirred at 0° C. for 30 min. The phases were separated and the aqueous layer was extracted with EtOAc (2×200 mL) and CH$_2$Cl$_2$ (2×100 mL). The organic layers were combined, washed with brine (1×300 mL), dried (Na$_2$SO$_4$), and concentrated to yield the title compound as a pale yellow oil.

HPLC: R$_T$=4.69 min

MS (ESI): calcd. for C$_{19}$H$_{29}$N$_3$O$_2$, 331.23; m/z found, 332.2 (M+1)

$^1$H NMR (CDCl$_3$): 7.36 (s, 4H), 3.79 (br s, 2H), 3.71 (t, J=4.7 Hz, 4H), 3.51 (s, 2H), 3.44 (br s, 2H), 2.76-2.69 (m, 1H), 2.59 (br s, 2H), 2.44 (t, J=4.4 Hz, 6H), 1.05 (d, J=6.5 Hz, 6H).

EXAMPLE 18

(4-Isopropyl-piperazin-1-yl)-(4-morpholin-4-ylmethyl-phenyl)-methanone, bis-maleate salt

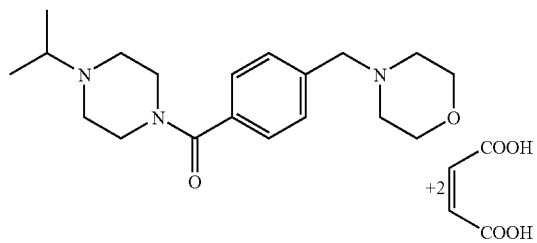

To a solution of (4-isopropyl-piperazin-1-yl)-(4-morpholin-4-ylmethyl -phenyl)-methanone (34.0 g, 102.7 mmol) in absolute EtOH (200 mL) was added, via an addition funnel, a solution of maleic acid (23.9 g, 206 mmol) in absolute EtOH (200 mL) over 15 min. The resulting suspension was stirred at room temperature for 30 min, at 75° C. for 1 h, and was then allowed to cool to room temperature over 16 h. The reaction mixture was cooled further to 0° C. and was stirred for 2 h. The reaction mixture was diluted with Et$_2$O (50 mL) and stirred for 30 min. The resulting precipitate was collected by suction filtration, washed with cold EtOH/Et$_2$O (4:1,100 mL×2), and dried in a vacuum oven at 40° C. for 20 h to yield the title compound as crude material, as a white solid.

A suspension of the crude (4-isopropyl-piperazin-1-yl)-(4-morpholin-4-ylmethyl-phenyl)-methanone, bis-maleate salt (90.5 g) in absolute EtOH (905 mL) was heated at 75° C. for 1 h, and the resulting solution was filtered through a fine porosity glass frit. The filtrate was cooled to room temperature over 20 h, with stirring. The resulting suspension was cooled to 0° C. for 2 h, and the precipitate was collected by suction filtration and washed with Et$_2$O (2×200 mL). The solids were dried in a vacuum oven at 40° C. for 20 h to yield the title compound as a white crystalline solid.

MP: 148-150° C.

MS (ESI): calcd. for C$_{19}$H$_{29}$N$_3$O$_2$, 331.23; m/z found, 332.2 (M+1)

$^1$H NMR (CD$_3$OD): 7.54-7.48 (m, 4H), 6.26 (s, 4H), 4.23 (s, 2H), 3.85 (br m, 8H), 3.56 (br s, 1H), 3.42-3.32 (br s, 4H), 3.13 (br s, 4H), 1.38 (d, J=6.6 Hz, 6H). Anal. calcd. for C$_{27}$H$_{37}$N$_3$O$_{10}$: C, 57.54; H, 6.62; N, 7.46. Found: C, 57.52; H, 6.73; N, 7.54.

EXAMPLE 19

4-Formyl-benzoyl chloride

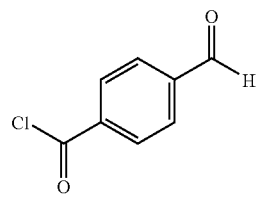

A solution of 4-carboxybenzaldehyde (30.0 g, 0.200 mol) in toluene (300 mL) was treated with thionyl chloride (28.6 g, 0.240 mol) and DMF (1.0 mL). The reaction mixture was heated at 100° C. for 2 h, during which time the solids dissolved to yield a pale yellow colored solution. The reaction mixture was cooled to 0° C. to yield a solution of the title compound in toluene, which was used without further manipulation.

EXAMPLE 20

Hydroxy-[4-(4-isopropyl-piperazine-1-carbonyl)-phenyl]-methanesulfonic acid sodium salt

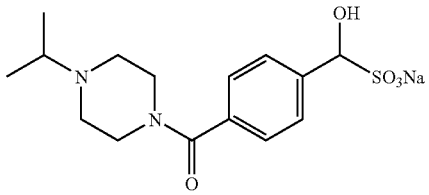

A solution of NaOH (24.0 g, 0.600 mol) in de-ionized H$_2$O (240 mL) and toluene (60 mL) at 0° C. was treated with isopropyl piperazine dihydrochloride salt (39.0 g, 194 mmol). The resulting biphasic solution was stirred at 0° C. for 30 min. A solution of 4-formyl-benzoyl chloride in toluene was added in a slow stream via an addition funnel over 1 h, with vigorous mechanical agitation. The mixture was allowed to warm to room temperature over 16 h, then cooled to 0° C., and the pH adjusted to 10 with 1 N NaOH. The phases were separated and the aqueous layer was extracted with toluene (2×200 mL). The organic layers were combined, washed with brine (200 mL), and concentrated to yield 4-(4-isopropyl-piperazine-1-carbonyl)-benzaldehyde (52.5 g, mass balance 101%) as a pale, yellow-brown oil. The oil was dissolved in EtOH (600 mL) and, with vigorous mechanical agitation, was treated with a solution of NaHSO$_3$ (23.1 g, 222 mmol) in de-ionized H$_2$O (50 mL) which was added via an addition funnel over 30 min. The resulting mixture was stirred at room temperature for 48 h, and then cooled to 0° C. Methyl-tert-butyl ether (500 mL) was added and the resulting the slurry was stirred for 30 min. The precipitate was collected by suction filtration through a medium porosity glass frit, washed with cold EtOH/EtOAc (5:1, 3×60 mL). The solids were dried under vacuum for 2 h, then at 40° C. in a vacuum oven for 16 h to yield the title compound as a white solid.

HPLC: RT=5.43 min
MP: 275° C. (dec.)

EXAMPLE 21

(4-Isopropyl-piperazin-1-yl)-(4-piperidin-1-ylmethyl-phenyl)-methanone

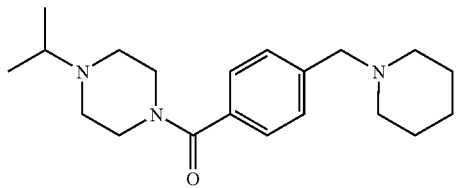

A mixture of hydroxy-[4-(4-isopropyl-piperazine-1-carbonyl)-phenyl]-methanesulfonic acid sodium salt (54.6 g, 0.150 mol), piperidine (28.0 g, 0.330 mol), and Montmorillonite-K10 (10.9 g, 20% by wt. relative to starting material) in dichloroethane (820 mL) was stirred at room temperature for 16 h. NaBH(OAc)$_3$ (44.5 g, 210.0 mmol) was added in portions over 1 h, and the resulting suspension was stirred at room temperature for 5 h. Diatomaceous earth (5.4 g) was added and the suspension was stirred for an additional 30 min. The reaction mixture was filtered through a pad of diatomaceous earth, rinsing with dichloroethane (2×100 mL). The filtrate was washed with 1 N NaOH (2×200 mL). The aqueous layers were combined and back-extracted with dichloroethane (2×100 mL). The organic layers were combined, dried (Na$_2$SO$_4$), and concentrated to yield the title compound as its corresponding free base, as a pale yellow oil.

HPLC: R$_T$=4.76 min
MS (ESI): calcd. for C$_{20}$H$_{31}$N$_3$O, 329.25; m/z found, 330.2 (M+1)
$^1$H NMR (CDCl$_3$): 7.35 (s, 4H), 3.79 (br s, 2H), 3.48 (br s, 2H), 3.45 (br s, 2H), 2.72 (m, 1H), 2.59 (br s, 2H), 2.45 (br s, 2H), 2.38 (br s, 4H), 1.60-1.55 (m, 4H), 1.48-1.40 (m, 2H), 1.06 (d, J=6.3 Hz, 6H).

EXAMPLE 22

(4-Isopropyl-piperazin-1-yl)-(4-piperidin-1-ylmethyl-phenyl)-methanone, bis-maleate salt

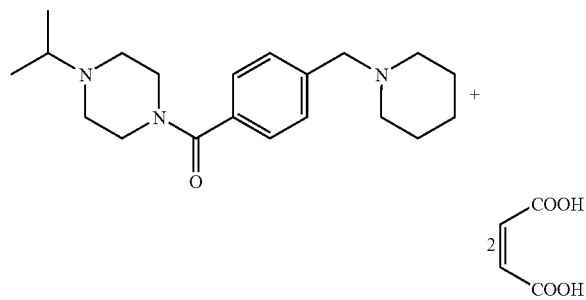

To a mechanically agitated solution of (4-isopropyl-piperazin-1-yl)-(4-piperidin-1-ylmethyl-phenyl)-methanone (40.0 g, 122 mmol) in absolute EtOH (800 mL) was added, via an addition funnel, a solution of maleic acid (28.2 g, 243 mmol) in absolute EtOH (200 mL) over 30 min. The resulting suspension was stirred at room temperature for 16 h, then diluted with Et$_2$O (200 mL), cooled to 0° C., and stirred for 2 h. The precipitate was collected by suction filtration, washed with cold EtOH/Et$_2$O (4:1, 3×100 mL). The solids were dried under vacuum to yield crude title compound as a white solid.

A mechanically agitated suspension of the crude material (4-isopropyl-piperazin-1-yl)-(4-piperidin-1-ylmethyl-phenyl)-methanone, bis-maleate salt) (89.0 g) in absolute EtOH (1780 mL) was heated at 75° C. for 1 h. The resulting pale yellow solution was allowed to cool to room temperature with stirring over 36 h, then diluted with Et$_2$O (220 mL), cooled to 0° C., and stirred for 3 h. The precipitate was collected by suction filtration, washed with Et$_2$O (2×100 mL). The solids were dried under vacuum for 16 h to yield the title compound as a white crystalline solid.

MP: 165-167° C.
MS (ESI): calcd. for C$_{20}$H$_{31}$N$_3$O, 329.25; m/z found, 330.2 (M+1)
Anal. calcd. for C$_{28}$H$_{39}$N$_3$O$_9$: C, 59.88; H, 7.00; N, 7.48. Found: C, 59.56; H, 7.29; N, 7.40.

EXAMPLE 23

Representative Examples of Reductive Amination of Bisulfite Adducts

Method A

A suspension of benzadehyde bisulfite adduct as listed in Table 3 below (5.0 mmol), Montmorillonite-K10 (0.21 g), and morpholine (10.0 mmol) in dichloroethane (20 mL) was stirred at room temperature for 45 min. NaBH(OAc)$_3$ (7.0 mmol) was added portion-wise over approximately 30 min. After 4 h, the reaction mixture was diluted with EtOAc (80 mL), filtered, and washed with 1N NaOH (25 mL) followed by brine (25 mL). The organic layer was dried (MgSO$_4$) and concentrated to yield 4-benzyl-morpholine as an oil. In cases where Montmorillonite K-10 was not used, the filtration step after completion of reaction was not necessary.

General Purification Method

The crude product from Method A was dissolved in EtOAc (50 mL) and the organic layer was extracted with 1.5 N HCl (25 mL). The aqueous layer was basified to ca. pH 12 with 1 N NaOH, and extracted with EtOAc (3×50 mL). The combined organic layers were dried (MgSO$_4$) and concentrated to yield the desired product (HPLC Purity >97%).

Method B

A suspension of cyclohexanecarboxaldehyde bisulfite adduct (5.0 mmol) and Et$_3$ N (5.5 mmol) in dichloroethane (20 mL) was stirred at room temperature for 15 min. The suspension was treated with N-methylbenzylamine (5.5 mmol) and was stirred for 45 min. NaBH(OAc)$_3$ (7.0 mmol) was added portion-wise over approximately 30 min. After 16 h, the reaction mixture was diluted with EtOAc (80 mL), and was washed with 1 N NaOH (25 mL) followed by brine (25 mL). The organic layer was dried (MgSO$_4$) and concentrated to yield benzyl-cyclohexylmethyl-methyl-amine as an oil. The crude material was purified by the General Purification Method as described above.

Table 9 below lists reductive amination reactions which were completed on representative bisulfite compounds. The column entitled "Reagents" list the reagents or reagent combination used in the reaction to yielded the desired product as listed.

TABLE 9

Representative Examples of Reductive Amination $$\underset{R}{HO\diagdown\!\!\!\diagup SO_3Na} \longrightarrow \underset{R}{\diagup\!\!\!\diagdown NR_1R_2}$$

| Bisulfite Reagent | Method | Reagents | Product |
|---|---|---|---|
| PhCH(OH)SO₃Na | A | Morpholine (2.0 equiv.) | benzyl morpholine |
| PhCH(OH)SO₃Na | A | Montmorillonite K-10 + Morpholine (2.0 equiv.) | benzyl morpholine |
| PhCH(OH)SO₃Na | A | Piperidine (2.0 equiv.) | benzyl piperidine |
| PhCH(OH)SO₃Na | A | Montmorillonite K-10 + Piperidine (2.0 equiv.) | benzyl piperidine |
| PhCH(OH)SO₃Na | B | TEA (1.1 equiv.) + Piperidine (1.1 equiv.) | benzyl piperidine |
| 4-EtC₆H₄CH(OH)SO₃Na | A | Pyrrrolidine (2.0 equiv.) | 4-ethylbenzyl pyrrolidine |
| 4-EtC₆H₄CH(OH)SO₃Na | B | TEA (1.1 equiv) + Pyrrolidine (1.1 equiv.) | 4-ethylbenzyl pyrrolidine |

TABLE 9-continued

Representative Examples of Reductive Amination $$\underset{R}{HO\diagdown\diagup SO_3Na} \longrightarrow \underset{R}{\diagdown NR_1R_2}$$

| Bisulfite Reagent | Method | Reagents | Product |
|---|---|---|---|
| HO-CH(SO₃Na)-C₆H₄-OCH₃ (para) | B | TEA (1.1 equiv.) + Pyrrolidine (1.1 equiv.) | H₃CO-C₆H₄-CH₂-N(pyrrolidine) |
| HO-CH(SO₃Na)-C₆H₄-OCH₃ (para) | B | TEA (1.1 equiv.) + Diethylamine (1.1 equiv.) | H₃CO-C₆H₄-CH₂-N(Et)₂ |
| NaO₃S-CH(OH)-CH₂-CH₂-C₆H₅ | B | TEA (1.1 equiv.) + Pyrrolidine (1.1 equiv.) | C₆H₅-CH₂-CH₂-CH₂-N(pyrrolidine) |
| NaO₃S-CH(OH)-CH₂-CH₂-C₆H₅ | B | TEA (1.1 equiv.) + Morpholine (1.1 Equiv.) | C₆H₅-CH₂-CH₂-CH₂-N(morpholine) |
| HO-CH(SO₃Na)-C₆H₁₁ (cyclohexyl) | B | TEA (1.1 equiv.) + N-Methylbenzylamine | C₆H₁₁-CH₂-N(CH₃)-CH₂-C₆H₅ |

TABLE 9-continued

Representative Examples of Reductive Amination

| Bisulfite Reagent | Method | Reagents | Product |
|---|---|---|---|
| (cyclopentyl-CH₂-CH(OH)-SO₃Na) | B | TEA (1.2 equiv.) + 3-[4-(1-Acetyl-2,3-dihydro-1H-indol-6-yl)-3-oxo-4-piperidin-4-yl-butyl]-benzonitrile (0.8 Equiv.) | (product structure with cyclopentyl, piperidine, indoline-acetyl, and benzonitrile groups) |
| (4-(4-isopropylpiperazine-1-carbonyl)phenyl)-CH(OH)-SO₃Na | A | Morpholine (2.0 equiv.) | (4-isopropylpiperazine-carbonyl-phenyl-CH₂-morpholine) |
| (4-(4-isopropylpiperazine-1-carbonyl)phenyl)-CH(OH)-SO₃Na | B | TEA (1.1 equiv.); Morpholine (1.1 equiv.) | (4-isopropylpiperazine-carbonyl-phenyl-CH₂-morpholine) |

EXAMPLE 24

(4-Cyclopropyl-piperazin-1-yl)-(4-morpholin-4-ylmethyl-phenyl)-methanone

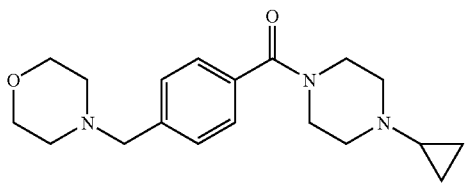

Step A. 4-(4-Formyl-benzoyl)-piperazine-1-carboxylic acid tert-butyl ester

A suspension of 4-carboxybenzaldehyde (3.10 g) in CH$_2$Cl$_2$ was treated sequentially with piperazine-1-carboxylic acid tert-butyl ester (3.6 g), EDCl (3.86 g), HOBt (2.68 g), and 4-dimethylaminopyridine (~0.020 g). After 18 h, the mixture was extracted with 1 N NaOH and then with 1 N HCl. The organic layer was dried (Na$_2$SO$_4$) and concentrated to yield the title compound.

MS (ESI): mass calcd. for C$_{17}$H$_{22}$N$_2$O$_4$, 318.16; m/z found, 219.3 [(M−100)+H]$^+$ $^1$H NMR (CDCl$_3$): 10.04 (s, 1H), 7.93 (d, J=8.2, 2H), 7.54 (d, J=8.1, 2H), 3.82-3.67 (m, 2H), 3.58-3.30 (m, 6H), 1.46 (s, 9H).

Step B. 4-(4-Morpholin-4-ylmethyl-benzoyl)-piperazine-1-carboxylic acid tert-butyl ester A solution of 4-(4-formyl-benzoyl)-piperazine-1-carboxylic acid tert-butyl ester (2.06 g) in methanol (100 mL) was treated with morpholine (4 mL) and NaBH(OAc)$_3$ (6.98 g, in portions over 1 h). After 3 h, the mixture was diluted with saturated aquoues NaHCO$_3$ and extracted with CH$_2$Cl$_2$. The organic layer was dried (Na$_2$SO$_4$) and concentrated. The residue was purified by column chromatography (SiO$_2$) to yield the title compound.

MS (ESI): mass calcd. for C$_{21}$H$_{31}$N$_3$O$_4$, 389.23; m/z found, 390.4 [M+H]$^+$.

$^1$H NMR (CDCl$_3$): 7.39-7.33 (m, 4H), 3.75-3.66 (m, 6H), 3.50 (s, 2H), 3.51-3.33 (m, 6H), 2.45-2.41(m, 4H), 1.46 (s, 9H).

Step C. (4-Morpholin-4-ylmethyl-phenyl)-piperazin-1-yl-methanone

A solution of 4-(4-morpholin-4-ylmethyl-benzoyl)-piperazine-1-carboxylic acid tert-butyl ester (1.163 g) in CH$_2$Cl$_2$ (10 mL) was treated with trifluoroacetic acid (~4 mL). After 30 min, additional trifluoroacetic acid (5 mL) was added, and the mixture was stirred for a further 2 h. The mixture was diluted with saturated aquoues NaHCO$_3$ and extracted with CH$_2$Cl$_2$. The organic layer was dried (Na$_2$SO$_4$) and concentrated. The residue was purified by column chromatography (SiO$_2$) to yield the title compound.

MS (ESI): mass calcd. for C$_{16}$H$_{23}$N$_3$O$_2$, 289.18; m/z found, 290.4 [M+H]$^+$ $^1$H NMR (CDCl$_3$): 7.41-7.35 (m, 4H), 3.95-3.70 (m, 6H), 3.52 (s, 2H), 3.09-2.80 (m, 6H), 2.49-2.42 (m, 4H).

Step D. (4-Cyclopropyl-piperazin-1-yl)-(4-morpholin-4-ylmethyl-phenyl)-methanone A solution of (4-morpholin-4-ylmethyl-phenyl)-piperazin-1-yl-methanone (0.128 g) in methanol (7.5 mL) was treated with (1-ethoxy-cyclopropoxy)-trimethyl-silane (1.5 mL), acetic acid (0.2 mL), and NaBH$_3$CN (~400 mg). The mixture was heated at 60° C. for 18 h, and then was cooled to room temperature and concentrated. The residue was diluted with 1 N NaOH and extracted with CH$_2$Cl$_2$. The organic layer was dried (Na$_2$SO$_4$) and concentrated. The residue was purified by column chromatography (SiO$_2$) to yield the title compound.

MS (ESI): mass calcd. for C$_{19}$H$_{27}$N$_3$O$_2$, 329.21; m/z found, 330.4 [M+H]$^+$ $^1$H NMR (CDCl$_3$): 7.36 (s, 4H), 3.79-3.68 (m, 6H), 3.50 (s, 2H), 3.44-3.32 (m, 2H), 2.74-2.61(m, 2H), 2.60-2.50 (s, 2H), 2.45-2.40 (m, 4H), 1.66-1.62 (m, 1H), 0.49-0.44 (m, 2H), 0.44-0.39 (m, 2H).

EXAMPLE 25

(4-Cyclopropyl-piperazin-1-yl)-(4-morpholin-4-ylmethyl-phenyl)-methanone

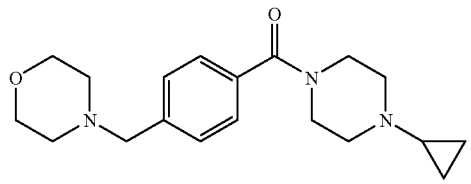

Step A. tert-Butyl 4-cyclopropylpiperazine-1-carboxylate

A mixture of tert-butyl piperazine-1-carboxylate (75.0 g), THF (500 mL), methanol (500 mL), [(1-ethoxycyclopropyl)oxy]trimethylsilane (161 mL), NaBH$_3$CN (38.0 g), and acetic acid (37 mL) was heated at 60° C. for 5 h. The mixture was cooled to room temperature, treated with water (30 mL) and stirred for 5 min. The mixture was then treated with 1 N NaOH (130 mL) and was further stirred for 15 min. The mixture was concentrated, and the remaining aqueous solution was extracted with CH$_2$Cl$_2$ (500 mL). The organic layer was washed with 1 N NaOH (500 mL). The combined aqueous layers were extracted with CH$_2$Cl$_2$ (150 mL). The combined organic layers were washed with brine (400 mL), dried (Na$_2$SO$_4$), and concentrated to yield the title compound as a white solid.

MS (ESI): mass calcd. for C$_{12}$H$_{22}$N$_2$O$_2$, 226.17; m/z found, 227.2 [M+H$^+$]

$^1$H NMR (400 MHz, CDCl$_3$): 3.39 (t, J=5.0 Hz, 4H), 2.55 (t, J=4.9 Hz, 4H), 1.60 (ddd, J=10.3, 6.5, 3.8 Hz, 1H), 1.46 (s, 9H), 0.49-0.38 (m, 4H).

Step B. 1-Cyclopropylpiperazine dihydrochloride

A solution of tert-butyl 4-cyclopropylpiperazine-1-carboxylate (92 g) in 1,4-dioxin (200 mL) was treated with HCl (4 M in 1,4-dioxin, 500 mL) over 10 min while maintaining the temperature below 40° C. After the addition was complete, the mixture was heated at 45° C. for 9 h and then was cooled to room temperature. The thick suspension was diluted with hexanes (400 mL) and was cooled to 10° C. The resulting solid was collected by filtration, washed with hexanes, and dried to yield the title compound as a white solid.

MS (ESI): mass calcd. for $C_7H_{14}N_2$, 126.12; m/z found, 127.0 [M+H$^+$]

$^1$H NMR (400 MHz, D$_2$O): 3.65 (br t, J=4.7 Hz, 4H), 3.47 (br t, J=5.5 Hz, 4H), 2.85 (br quintet, J=5.8 Hz, 1H), 0.94 (br s, 2H), 0.92 (br s, 2H).

Step C. 4-(4-Cyclopropyl-piperazine-1-carbonyl)-benzaldehyde

A mixture of 4-formyl-benzoic acid (54.4 g), toluene (500 mL), DMF (3.6 mL), and thionyl chloride (30.4 mL) was heated at 60° C. for 2 h and then was cooled to 5° C. In a separate flask, a 5° C. mixture of NaOH (50.7 g), water (550 mL), and toluene (150 mL) was treated with 1-cyclopropyl-piperazine dihydrochloride (70.0 g) in portions while the temperature was maintained below 10° C. After the addition was complete, the mixture was cooled to 5° C. and treated with the crude acyl chloride solution prepared as above at a rate such that the temperature did not exceed 10° C. After the addition was complete, the mixture was allowed to warm to room temperature and was stirred overnight. The biphasic mixture was basified to pH~10 with 1 N NaOH (300 mL). The layers were separated and the aqueous layer was extracted with toluene (100 mL×2). The combined organic layers were washed with brine (200 mL), dried (Na$_2$SO$_4$), and concentrated to yield the title compound as pale yellow viscous oil.

HPLC: R$_T$=5.19 min

MS (ESI): mass calcd. for $C_{15}H_{18}N_2O_2$, 258.14; m/z found, 258.9 [M+H$^+$]

$^1$H NMR (400 MHz, CDCl$_3$): 10.1(s, 1H), 7.94 (pseudo d, J=8.2 Hz, 2H), 7.56 (pseudo d, J=8.1 Hz, 2H), 3.77 (br s, 2H), 3.33 (br s, 2H), 2.71(br s, 2H), 2.55 (br s, 2H), 1.66 (ddd, J=10.2, 6.6, 3.7 Hz, 1H), 0.52-0.46 (m, 2H), 0.45-0.40 (br s, 2H).

Step D. (4-Cyclopropyl-piperazin-1-yl)-(4-morpholin-4-ylmethyl-phenyl)-methanone To a solution of 4-(4-cyclopropyl-piperazine-1-carbonyl)-benzaldehyde (56.0 g) in 1,2-dichloroethane (550 mL) was added morpholine (37.8 mL) dropwise over 5 min. The mixture was cooled to 10° C. and was treated with NaBH(OAc)$_3$ (64.3 g) in portions over 1 h. After a further 2 h, the mixture was warmed to room temperature, and a water bath was used to keep the temperature below 20° C. After 18 h, water (60 mL) was added while the temperature was kept under 20° C. by the addition of small amounts of ice. After 20 min, the mixture was basified to pH~10 with 1 N NaOH (450 mL) and the mixture was stirred for 10 min. The layers were separated, and the organic layer was washed with 1 N NaOH (150 mL). The combined aqueous layers were extracted with CH$_2$Cl$_2$ (200 mL). The combined organic layers were washed with brine (200 mL), dried (Na$_2$SO$_4$), and concentrated to yield the title compound as pale yellow viscous oil.

HPLC: R$_T$=4.39 min

MS (ESI): mass calcd. for $C_{19}H_{27}N_3O_2$, 329.21; m/z found, 330.2 [M+H$^+$]

$^1$H NMR (400 MHz, CDCl$_3$): 7.35 (br s, 4H), 3.73 (br s, 2H), 3.69 (t, J=4.6 Hz, 4H), 3.50 (s, 2H), 3.37 (br s, 2H), 2.67 (br s, 2H), 2.53 (br s, 2H), 2.43 (t, J=4.2 Hz, 4H), 1.63 (ddd, J=10.3, 6.7, 3.7 Hz, 1H), 0.49-0.43 (m, 2H), 0.42-0.39 (br s, 2H).

$^{13}$C NMR (101 MHz, CDCl$_3$): 170.6, 140.0, 135.1, 129.5, 127.5, 67.4, 63.4, 54.0, 38.7, 6.3.

EXAMPLE 26

(4-Cyclopropyl-piperazin-1-yl)-(4-morpholin-4-ylmethyl-phenyl)-methanone dihydrochloride salt

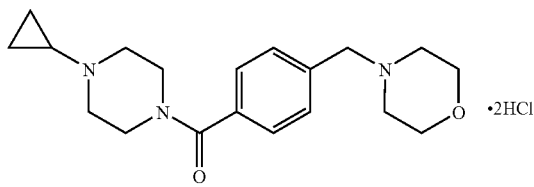

A solution of (4-cyclopropyl-piperazin-1-yl)-(4-morpholin-4-ylmethyl-phenyl)-methanone (68.0 g) in ethanol (400 mL) was heated to 60° C. and treated with concentrated HCl (37.8 mL) dropwise over 40 min. A precipitate started to form after ~20 mL of HCl had been added. After the addition was complete, the thick suspension was slowly cooled to 20° C. over 3 h. The solid was collected by filtration, washed with ethanol, and dried at 50° C. overnight in a vacuum oven to provide the title compound as a white solid.

HPLC: R$_T$=4.30 min

MS (ESI): mass calcd. for $C_{19}H_{27}N_3O_2$, 329.21; m/z found, 330.0 [M+H$^+$]

$^1$H NMR (400 MHz, D$_2$O): 7.64 (pseudo d, J=8.3 Hz, 2H), 7.58 (pseudo d, J=8.3 Hz, 2H), 4.44 (br s, 2H), 4.20-3.10 (m, 16H), 2.88 (ddd, J=11.2, 6.6, 4.8 Hz, 1H), 1.03-0.98 (m, 4H)

$^{13}$C NMR (101 MHz, D$_2$O): 172.1, 135.3, 132.2, 130.9, 128.0, 64.0, 60.5, 52.6, 52.4, 51.7, 44.8, 39.7, 39.5, 3.9.

EXAMPLE 27

(4-Isopropyl-piperazin-1-yl)-(4-morpholin-4-ylmethyl-phenyl)-methanone

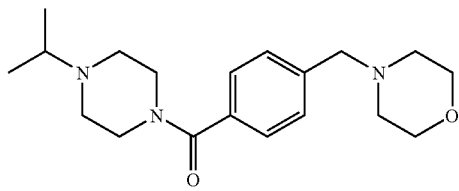

Preparation and analytical data for the title compound was presented in U.S. Patent Application Publication 2004-0110746 A1, published Apr. 21, 2005.

EXAMPLE 28

(4-Cyclobutyl-piperazin-1-yl)-(4-morpholin-4-ylm-ethyl-phenyl)-methanone

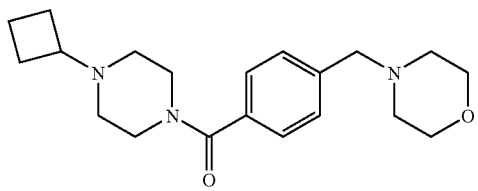

The title compound was prepared according to the methods described in Example 23 above.

EXAMPLE 29

Sodium [4-(4-Cyclopropyl-piperazine-1-carbonyl)-phenyl]-hydroxy-methanesulfonate

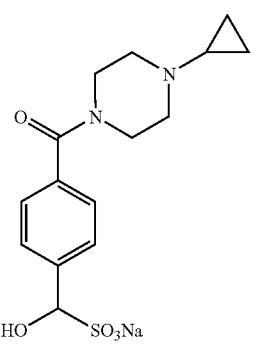

A 100 mL flask was charged with 4-(4-cyclopropyl-piperazine-1-carbonyl)-benzaldehyde (2.58 g, 10.0 mmol, 1.0 eq), acetonitrile (30 mL), and water (1.0 mL) under nitrogen atmosphere. The reaction mixture was heated to 50° C. A solution of $NaHSO_3$ (1.14 g, 11.0 mol, 1.1 eq) in water (2.0 mL) was added dropwise over 5 min. The reaction mixture was then cooled to 17° C. The product was collected by filtration as a white solid.

$^1$H-NMR (400 MHz, $D_2O$): δ 7.66 (pseudo d, 2H, J=8.1 Hz), 7.47 (pseudo d, 2H, J=8.2 Hz), 5.58 (s, 1H), 3.74 (br s, 2H), 3.47 (br s, 2H), 2.84 (br s, 2H), 2.69 (br s, 2H), 1.85 (tt, 1H, J=7.0, 3.8 Hz), 0.60-0.54 (m, 2H), 0.49-0.44 (m, 2H)

MS (ESI-): mass calculated for $C_{15}H_{19}N_2O_5S$, 339.1; m/z found, 339.0 [M−Na]$^-$.

EXAMPLE 30

As a specific embodiment of an oral composition, 100 mg of the compound prepared as in Example 6 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A process for the preparation of a compound of formula (Is)

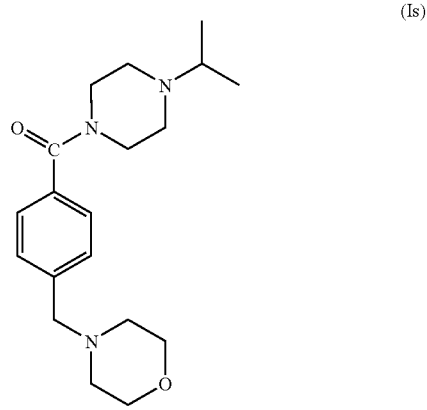

or a hydrate or pharmaceutically acceptable salt thereof comprising

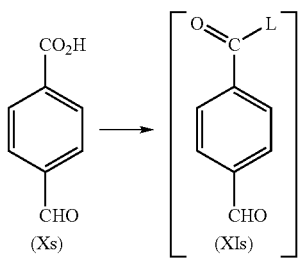

reacting a compound of formula (Xs); in a first organic solvent; to yield the corresponding compound of formula (XIs), wherein L is a leaving group; and wherein the compound of formula (XIs) is not isolated;

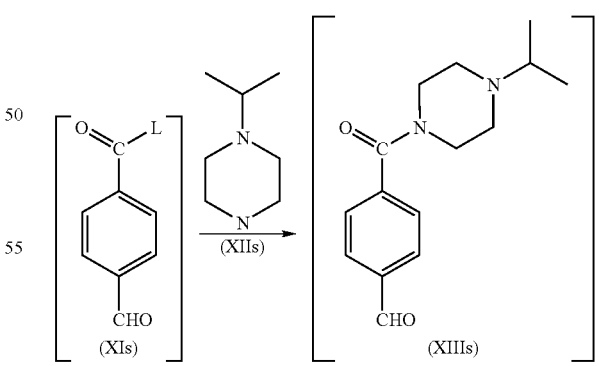

reacting the compound of formula (XIs) with a compound of formula (XIIs); in the presence of an organic or inorganic base; in a second organic solvent; to yield the corresponding compound of formula (XIIIs); wherein the compound of formula (XIIIs) is not isolated;

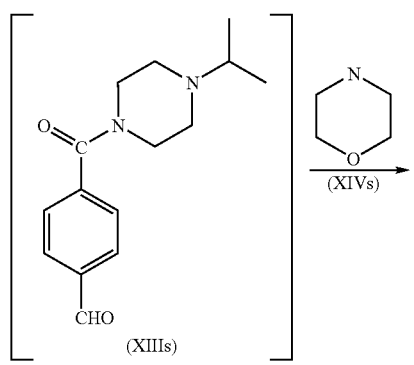

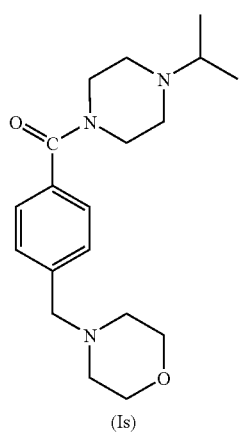

and reacting the compound of formula (XIIIs) with a compound of formula (XIVs); in the presence of a reducing agent; in a third organic solvent; to yield the corresponding compound of formula (Is);

wherein the first organic solvent, the second organic solvent and the third organic solvent are the same and optionally reacting the compound of formula (Is) to yield the corresponding hydrate or pharmaceutically acceptable salt of the compound of formula (Is).

2. A process as in claim 1, wherein L is chloro.

3. A process as in claim 1, wherein the compound of formula (XIIs) is present in an amount equal to about one equivalent.

4. A process as in claim 1, wherein the compound of formula (XIVs) is present in an amount greater than about one equivalent; and wherein the reducing agent is present in an amount in the range of from about 1 to about 2 equivalents.

5. A process as in claim 1, further comprising reacting the compound of formula (Is) to yield the corresponding pharmaceutically acceptable salt of the compound of formula (Is).

6. A process as in claim 5, wherein the pharmaceutically acceptable salt is selected from the group consisting of succinate, fumarate, maleate, hydrochlororide or hydrobromide salt.

7. A process as in claim 5, wherein the pharmaceutically acceptable salt is a mono-succinate salt.

* * * * *